United States Patent
Solie

(10) Patent No.: US 12,322,517 B2
(45) Date of Patent: Jun. 3, 2025

(54) MEDICAL SERVICES METHOD AND SYSTEM

(71) Applicant: OnMed LLC, Tampa, FL (US)

(72) Inventor: Leonard Solie, Tampa, FL (US)

(73) Assignee: OnMed LLC, Tampa, FL (US)

( * ) Notice: Subject to any disclaimer, the term of this patent is extended or adjusted under 35 U.S.C. 154(b) by 824 days.

(21) Appl. No.: 16/275,741

(22) Filed: Feb. 14, 2019

(65) Prior Publication Data

US 2020/0168346 A1 May 28, 2020

Related U.S. Application Data

(63) Continuation-in-part of application No. 13/777,864, filed on Feb. 26, 2013, now abandoned.

(60) Provisional application No. 61/606,095, filed on Mar. 2, 2012.

(51) Int. Cl.
| | | |
|---|---|---|
| *G16H 80/00* | (2018.01) | |
| *G16H 10/60* | (2018.01) | |
| *G16H 50/20* | (2018.01) | |
| *G16H 15/00* | (2018.01) | |

(52) U.S. Cl.
CPC .............. *G16H 80/00* (2018.01); *G16H 10/60* (2018.01); *G16H 50/20* (2018.01); *G16H 15/00* (2018.01)

(58) Field of Classification Search
None
See application file for complete search history.

(56) References Cited

U.S. PATENT DOCUMENTS

| | | |
|---|---|---|
| 5,012,348 A | 4/1991 | Witzel |
| 5,773,767 A | 6/1998 | Collins, Jr. |
| 6,205,716 B1 | 3/2001 | Peltz |
| 7,986,369 B1 | 7/2011 | Burns |
| 9,179,051 B1 | 11/2015 | Stoudt |
| 9,449,148 B2 | 9/2016 | Holmes |

(Continued)

FOREIGN PATENT DOCUMENTS

| | | | |
|---|---|---|---|
| EP | 2940612 | 11/2015 | |
| WO | WO-02096339 A1 * | 12/2002 | ............. A61G 10/00 |
| WO | 2014002091 A2 | 1/2014 | |

OTHER PUBLICATIONS

O'Heir, J. (2013). HealthSpot forms new partnerships, unveils telehealth kiosk. Dealerscope, 55(3), 14. Retrieved from https://dialog.proquest.com/professional/docview/1349217489?accountid=131444 (Year: 2013).

(Continued)

*Primary Examiner* — Robert A Sorey
(74) *Attorney, Agent, or Firm* — Darrow Mustafa PC

(57) ABSTRACT

A medical services system and method supporting private and secure telemedicine sessions between a patient and a remote medical facility are provided including a medical services kiosk comprising a plurality of individual interior chambers, an inventory storage component, and other medical technology. The medical services system is configured to communicatively couple components within both the medical services kiosk and the remote medical facility so that information necessary for examining, treating, and diagnosing the patient is acquired and medical professionals are able to provide offsite instructions, prescriptions, and other medical related services to the patient in a manner that is convenient, timely, and efficient.

16 Claims, 26 Drawing Sheets

(56) References Cited

U.S. PATENT DOCUMENTS

| | | | |
|---|---|---|---|
| 9,723,273 B2 | 8/2017 | Child | |
| 9,763,271 B1* | 9/2017 | Gabel | G06Q 30/08 |
| 10,052,026 B1 | 8/2018 | Tran | |
| 2002/0104271 A1* | 8/2002 | Gallant | E04B 2/7448 |
| | | | 52/270 |
| 2002/0133544 A1* | 9/2002 | Aoike | G08B 3/1083 |
| | | | 715/761 |
| 2003/0178233 A1 | 9/2003 | Montagnino | |
| 2003/0216831 A1 | 11/2003 | Hart | |
| 2003/0233129 A1 | 12/2003 | Matos | |
| 2004/0090424 A1 | 5/2004 | Hurley | |
| 2004/0145676 A1 | 7/2004 | Lin | |
| 2005/0229834 A1 | 10/2005 | Wong | |
| 2005/0239037 A1 | 10/2005 | Lertsithichai | |
| 2006/0028717 A1 | 2/2006 | Dunn | |
| 2006/0143041 A1* | 6/2006 | Tipirneni | G06Q 10/10 |
| | | | 715/733 |
| 2006/0155589 A1 | 7/2006 | Lane | |
| 2007/0208241 A1 | 9/2007 | Drucker | |
| 2007/0212326 A1 | 9/2007 | Ochs | |
| 2007/0288265 A1 | 12/2007 | Quinian | |
| 2008/0005974 A1 | 1/2008 | Delgado Vazquez | |
| 2009/0089085 A1* | 4/2009 | Schoenberg | G16H 40/20 |
| | | | 705/2 |
| 2009/0137882 A1 | 5/2009 | Baudino | |
| 2009/0167838 A1 | 7/2009 | Poisner | |
| 2009/0233769 A1* | 9/2009 | Pryor | B60R 11/02 |
| | | | 482/8 |
| 2009/0240528 A1 | 9/2009 | Bluth | |
| 2009/0241177 A1* | 9/2009 | Bluth | A61B 5/02055 |
| | | | 380/255 |
| 2009/0276242 A1* | 11/2009 | Waisbren | G06Q 40/08 |
| | | | 705/26.1 |
| 2010/0130873 A1 | 5/2010 | Yuen | |
| 2011/0014955 A1 | 1/2011 | Kim | |
| 2011/0015934 A1 | 1/2011 | Rowe | |
| 2011/0122995 A1 | 5/2011 | Ferro | |
| 2011/0161100 A1 | 6/2011 | Peak | |
| 2011/0307265 A1 | 12/2011 | Bannis | |
| 2011/0315611 A1 | 12/2011 | Fulkerson | |
| 2012/0179479 A1 | 7/2012 | Waterson | |
| 2012/0253837 A1 | 10/2012 | Cashman | |
| 2012/0275167 A1 | 11/2012 | Scruggs | |
| 2012/0289850 A1 | 11/2012 | Xu | |
| 2013/0014985 A1 | 1/2013 | Ferrara | |
| 2013/0062127 A1 | 3/2013 | Pangrazio | |
| 2013/0172787 A1 | 7/2013 | Marovets | |
| 2013/0173287 A1 | 7/2013 | Cashman | |
| 2013/0186429 A1 | 7/2013 | Morita | |
| 2013/0297219 A1 | 11/2013 | Bangera | |
| 2014/0052463 A1 | 2/2014 | Cashman et al. | |
| 2014/0095196 A1 | 4/2014 | Waterson | |
| 2014/0139616 A1 | 5/2014 | Pinter | |
| 2015/0042822 A1 | 2/2015 | Le | |
| 2016/0085935 A1 | 3/2016 | Waterson et al. | |
| 2016/0105641 A1 | 4/2016 | Periyannan | |
| 2017/0186712 A1 | 7/2017 | Ehlinger | |
| 2017/0323070 A1 | 11/2017 | Hodge | |
| 2017/0374502 A1* | 12/2017 | Gabel | G06Q 50/26 |
| 2018/0192965 A1 | 7/2018 | Rose | |
| 2018/0328780 A1 | 11/2018 | Cochran | |
| 2021/0035400 A1 | 2/2021 | Flynn | |
| 2022/0277608 A1 | 9/2022 | Brandauer | |

OTHER PUBLICATIONS

W.-P. Lu, H. Leung and E. Estrada, "Transforming telemedicine for rural and urban communities Telemedicine 2.0—any doctor, any place, any time," The 12th IEEE International Conference one-Health Networking, Applications and Services, Lyon, France, 2010, pp. 379-385 (Year: 2010).

* cited by examiner

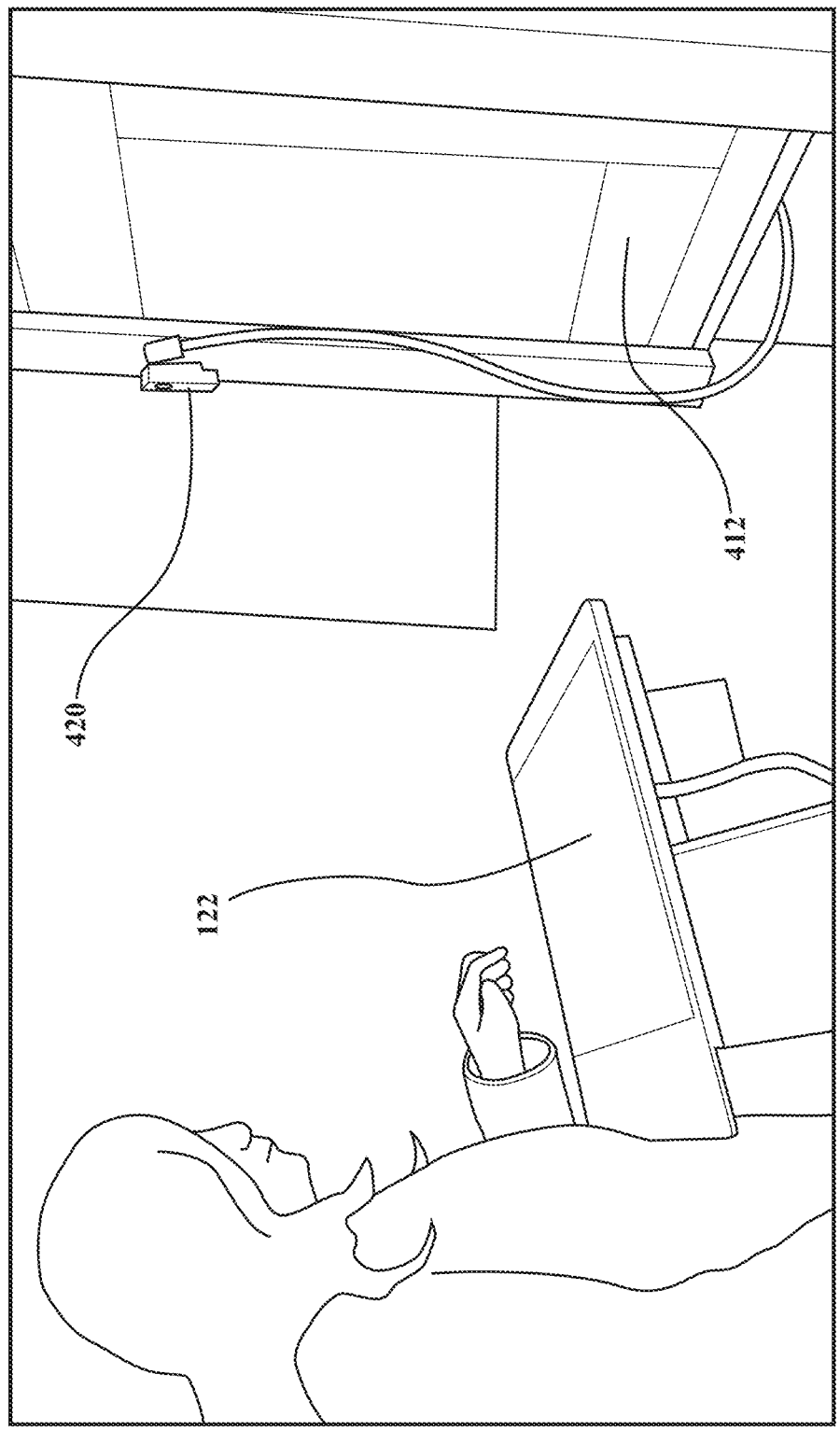

MEDICAL SERVICES METHOD AND SYSTEM

CROSS-REFERENCE TO RELATED APPLICATIONS

This application is a Continuation-In-Part of U.S. Utility patent application Ser. No. 13/777,864, filed on Feb. 26, 2013, which in turn claims the benefit of U.S. Provisional Patent Application Ser. No. 61/606,095, filed on Mar. 2, 2012, both of which are incorporated-by-reference herein it their entirety.

FIELD OF THE INVENTION

The present invention relates generally to a system and method for providing medical services, and more particularly, to a medical services system and method that assists medical services professionals in diagnosing and treating remote patients.

BACKGROUND OF THE INVENTION

Medical care is a need for every individual and every family. Many individuals have one or more physicians or other medical professionals that they see for wellness visits and for treatment of various illnesses and injuries. However, as the population continues to grow and healthcare continues to evolve, the need for doctors and health care providers continues to grow as well. As a result of this growth, medical facilities such as hospitals and doctors' offices are operating at maximum physical capacity. Since the population continues to grow and the need for doctors and health care providers is not expected to abate in the near or immediate future, there is a need for an alternative more efficient manner to see patients rather than physically seeing them on-site.

Medical facilities in general have been attempting to improve efficiency through utilizing technology. In particular, some aspects of patient care have been computerized through the use of electronic terminals interactively accessible to the patients. Currently, processes such as checking in and prescription refill requests may be handled entirely by digital mediums. These digital mediums may be in the form of specialized hardware and software for collecting, organizing, and updating information associated with patients.

Hospitals and medical clinics recently began utilizing interactive devices that allow patients to perform routine activities. The ability for patients to perform operations such as update personal information linked to their health profile, pay medical fees, and other various routine activities via these interactive devices has generated a significant increase in efficiency for medical facilities. However, patients are still required to be physically on-site in order for medical professionals to perform routine medical activities that are necessary to treat a patient such as measuring vital signs.

There have also been limitations regarding doctor and medical professional availability in the case when an individual requires immediate attention. For example, if an individual were to decide to visit a doctor or medical professional's office for a non-emergency the day of, then that individual would be classified as a "walk-in" if he or she did not have an appointment and would be subjected to a wait time associated with the current workload of the medical facility. The individual's only alternative would be to go the emergency room of a hospital for a non-emergency matter.

Recently, there have been developments in implementations of various systems and methods relating to telehealth and telemedicine. However, these systems and methods require a substantial amount of improvement in order for them to be nearly as efficient as the conventional practice of medicine.

Thus, there is a need for a medical services system that allows doctors and other medical professionals to examine, diagnose, and treat patients without requiring the patients to be physically present with the medical professional.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

SUMMARY OF THE INVENTION

The present invention is directed to a medical services system that is capable of generating a plurality of interactions between a user or patient and one or more medical professionals via a network comprising a plurality of client devices. The medical services system further comprises a patient station that satisfies the need for providing facilities for remote interaction with health care professionals in real time. The medical services system is configured to support examination, diagnosis, and treatment of a patient via establishing a tele-communicative connection between the patient and remote medical professionals via the network. The medical services system may include a plurality of components including, but not limited to, an interactive patient station, user-operable interfaces, screens, cameras, projectors, adjustable platforms, scales, kiosks, and medical equipment in order to assist remote medical professionals in examining, diagnosing, and treating patients within the interactive patient station. The medical services systems may be configured to interact with the patient in order to acquire information from the patient such as vital signs and other medically related measurements. A remote medical professional receives the acquired patient information and establishes a connection with the patient in order to render medical services to the patient. The medical services system will preferably interact with the patient and remote medical professionals by acquiring relevant information from the patient via components of the interactive patient station, allocating an applicable medical professional to receive the information, analyzing the patient based on the received information, and generating, by the medical professional, a set of one or more instructions to be executed by the medical services system.

Introducing a first embodiment of the invention, the present invention consists of a system for providing medical services, comprising:
  an enclosure comprising an interior space;
  at least one camera configured to support user interaction;
  an optical projector device;
  a visual user interface configured to support user interaction; and
  an adjustable screen display;
  wherein the camera, the optical projector device, the visual user interface, and the adjustable screen display are communicatively coupled.

Introducing a second embodiment of the invention, the present invention consists of a method for providing medical services, comprising:

collecting, from a first client device, a plurality of medical information from a patient;

receiving, by a second client device, the plurality of medical information;

wherein the second client device is associated with a medical services provider;

assigning an indicator to the medical services provider;

generating, by the medical services provider, a plurality of instructions configured to interact with the first client device;

Introducing a third embodiment of the invention, the present invention consists of one or more storage media storing instructions which, when executed by one or more processor, cause:

collecting, from a first client device, a plurality of medical information from a patient;

receiving, by a second client device, the plurality of medical information;

wherein the second client device is associated with a medical services provider;

assigning an indicator to the medical services provider;

generating, by the medical services provider, a plurality of instructions configured to interact with the first client device.

In another aspect, the medical services system comprises a plurality of platforms, cameras, and user-interfaces configured to be adjusted by the patient in order to support proper device placement based on the patient's height, width, comfort, preferences, etc. The platforms, cameras, and user-interfaces may be communicatively coupled and may be configured to rectify issues that would prevent the medical professional from being able to view or interpret medical information acquired from the patient. The platforms, cameras, user-interfaces, and other components within the patient station may be communicatively coupled to a first client device configured to interact with a second client device associated with the medical professional via the network.

In another aspect, the medical services system further comprises one or more cameras in a remote medical facility comprising a gooseneck or flexible connection. The one or more cameras may be configured to be attached to an extendable arm that supports adjustment of the camera to the eye-level of the medical professional and allows for varying positioning via swiveling or rotating. The cameras may be configured to interact with a retractable camera which comprises a retina scanner, thermal sensors, and an image processing unit configured to detect a position of the user's eyes and automatically readjust the position of the cameras to the patient's eye level.

In another aspect, the medical services system further comprises sensors, lighting, microphones, kiosks, computers/tablets, and a plurality of medical equipment including but not limited to thermometers, scales, blood pressure checkers, otoscopes, glucose monitors, etc., in order to acquire the necessary medical information from the patient and transmit the medical information to the remote medical professional.

In another aspect, the medical services system further comprises a plurality of ultraviolet sterilizers and an ultraviolet-based sanitation system configured to disinfect the interior of the medical services system and the medical equipment.

In another aspect, the medical services system comprises at least one medical kiosk comprising a retractable camera, ultraviolet sanitation components, automatic locking mechanisms, remote control mechanisms, an integrated scale, privacy windows, printers, and means to store and dispense medication and other medical equipment.

In another aspect, the medical services system may be configured to establish a secure communication portal between the patient and the medical professional via a network configured to access a plurality of data associated with the patient station and a remote medical facility and/or plurality of databases comprising medical data, such as patient health records, insurance information, and other medical information.

In another aspect, the medical services system comprises a documentation receiving device configured to receive forms of payment including, but not limited to, currency bills and credit/debit cards. The documentation receiving device comprises a means to scan identification and other forms of documentation in order to authenticate insurance coverage and other medically related documents.

As described herein, medical professional may include but is not limited to any doctor, pharmacist, nurse practitioner, nurse, nursing assistant, or any other individual who examines and treats or assists in the examination and treatment of patients for medical purposes.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 26 is a second example of the medical professional in the space within the remote medical facility of the medical services kiosk in which the techniques described may be practiced according to certain embodiments of the invention.

Like reference numerals refer to like parts throughout the several views of the drawings.

DETAILED DESCRIPTION

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
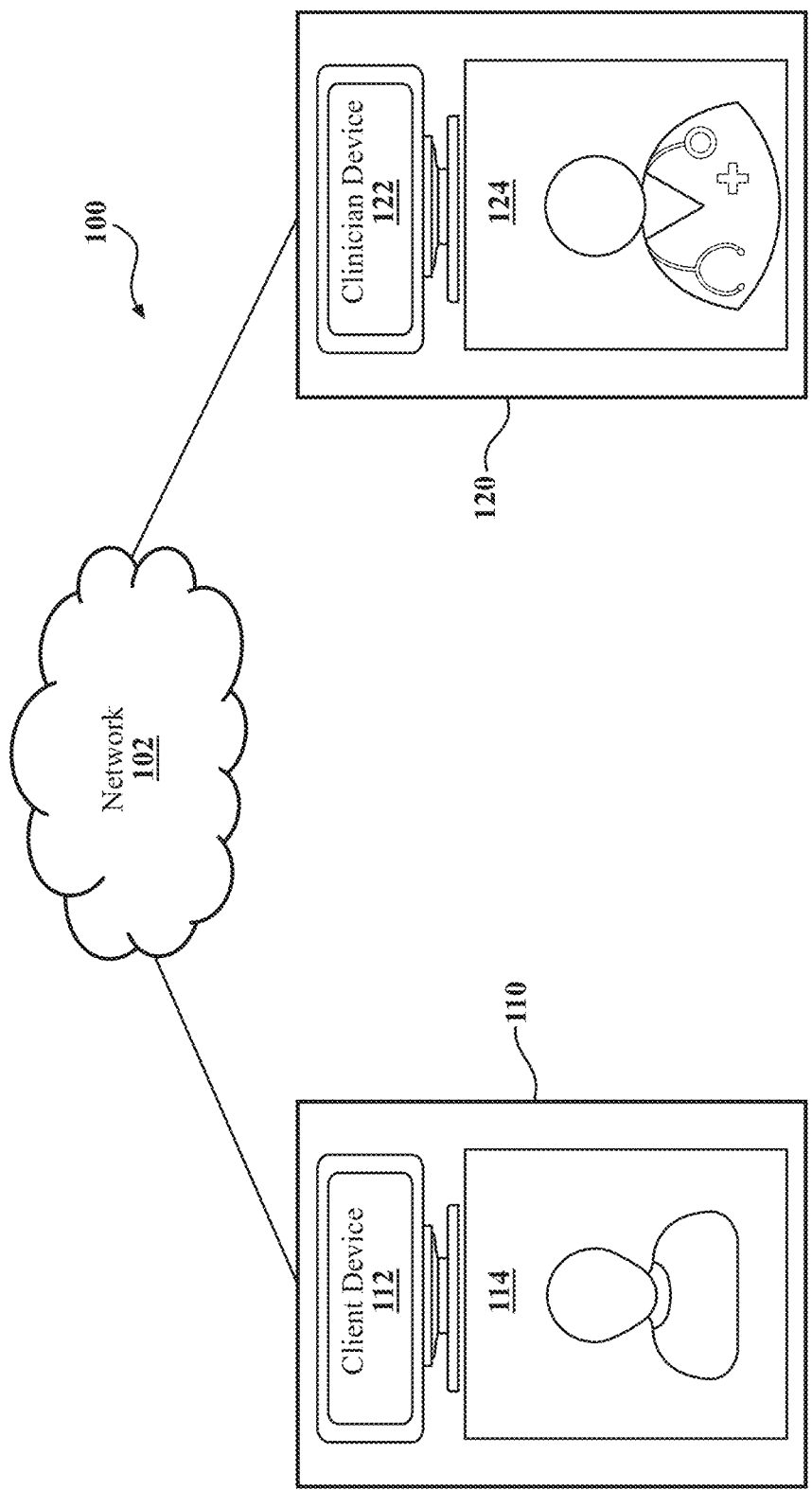
FIG. 1 is an example of a medical services system in which the techniques described in the present disclosure may be practiced according to certain embodiments of the invention.

The illustration of FIG. 1 depicts an example medical services system 100 in which the techniques described may be practiced according to certain embodiments. In one embodiment, the medical services system 100 may be implemented in hardware, software, or a combination of hardware and software. In some embodiment, the various components of the medical services system 100 are implemented at least partially by hardware at one or more computing devices, such as one or more hardware processors executing instructions stored in one or more memories for performing various functions described herein. For example, descriptions of various components (or modules) as described in this application may be interpreted by one of skill in the art as providing pseudocode, an informal high-level description of one or more computer structures. The descriptions of the components may be converted into software code, including code executable by an electronic processor. The medical services system 100 illustrates only one of many possible arrangements of components configured to perform the functionality described herein. Other arrangements may include fewer or different components, and the division of work between the components may vary depending on the arrangement.

As mentioned heretofore, FIG. 1 is an example system 100 for a medical services system, in an embodiment. The medical services system 100 includes a patient station 110 configured to house a patient client device 112 associated with a patient 114, and a remote medical facility 120 comprising a clinician station that includes a medical facility clinician device 122 associated with a medical professional 124, from which a remote medical assistance host company is operated. The patient station 110 and the remote medical facility 120 are communicatively coupled via a network 102. In one embodiment, the network 102 may be implemented by a network of communicatively coupled computing devices. The network 102 may utilize known security precautions such as encryption, passwords, limited Wi-Fi range, and the like. The remote medical facility 120 may comprise one or more of the medical facility clinician device 122 and the medical professional 124, and may be configured to access the network 102 in order to provide medical consultation and assistance. The network 102 may be configured to access computers and databases outside of the medical services system 100.

Although only the client device 112 and the medical facility clinician device 122 are depicted, the medical services system 100 may include multiple client devices 112 or medical facility clinician devices 122 that transmit activity events over the network 102. Examples of the client device 112 and the medical facility clinician device 122 include a laptop computer, a tablet computer, a smartphone, a desktop computer, and any other mechanism used to access networks and software. An example of software that executes on the client device 112 and the medical facility clinician device 122 includes a communication service that is configured to establish a secure session between the patient 114 and the medical professional 124 in order to conduct medical services.

Figure 2:
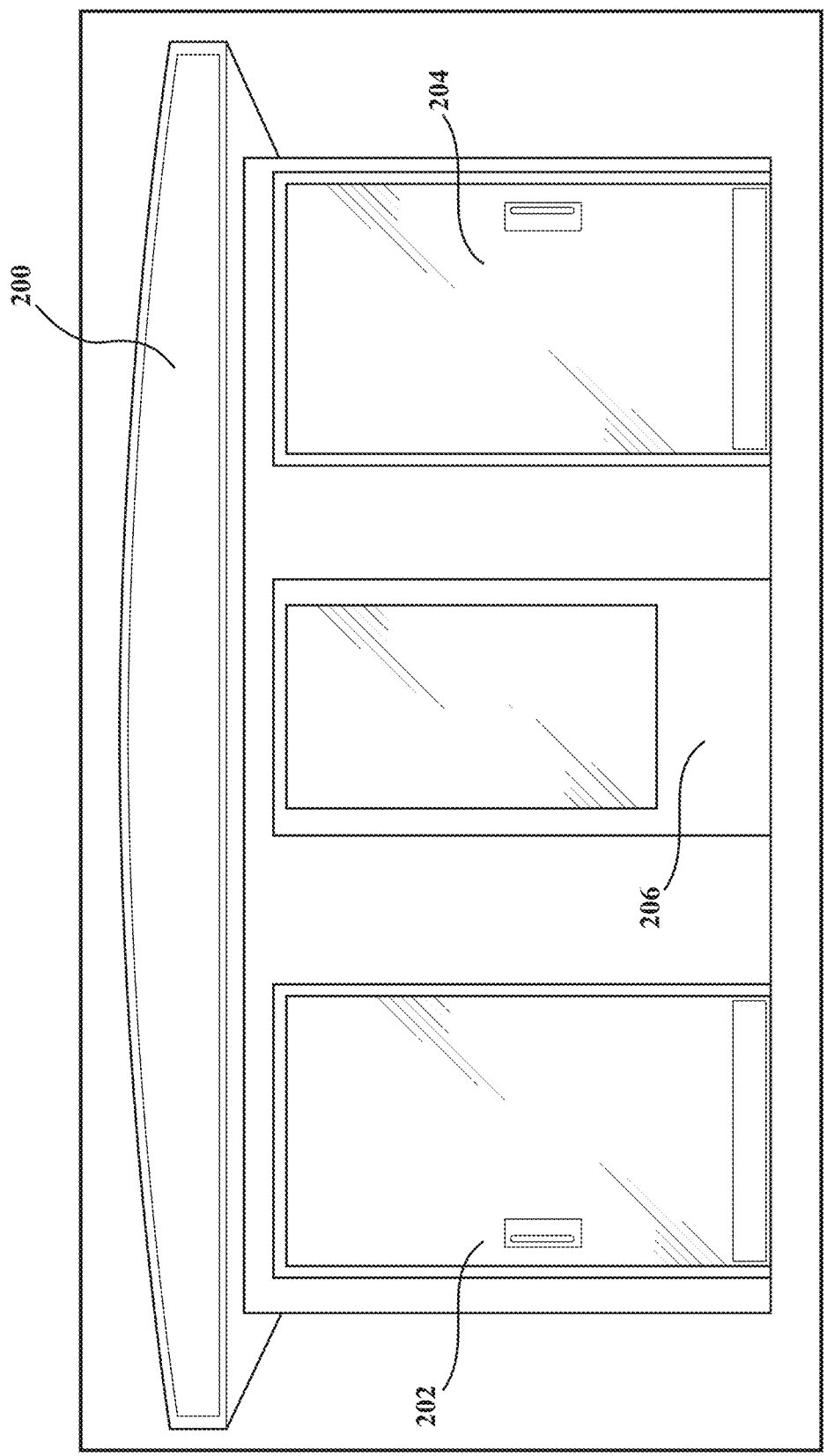
FIG. 2 is an example of the exterior of a medical services kiosk in which the techniques described may be practiced according to certain embodiments of the invention.
Figure 3:
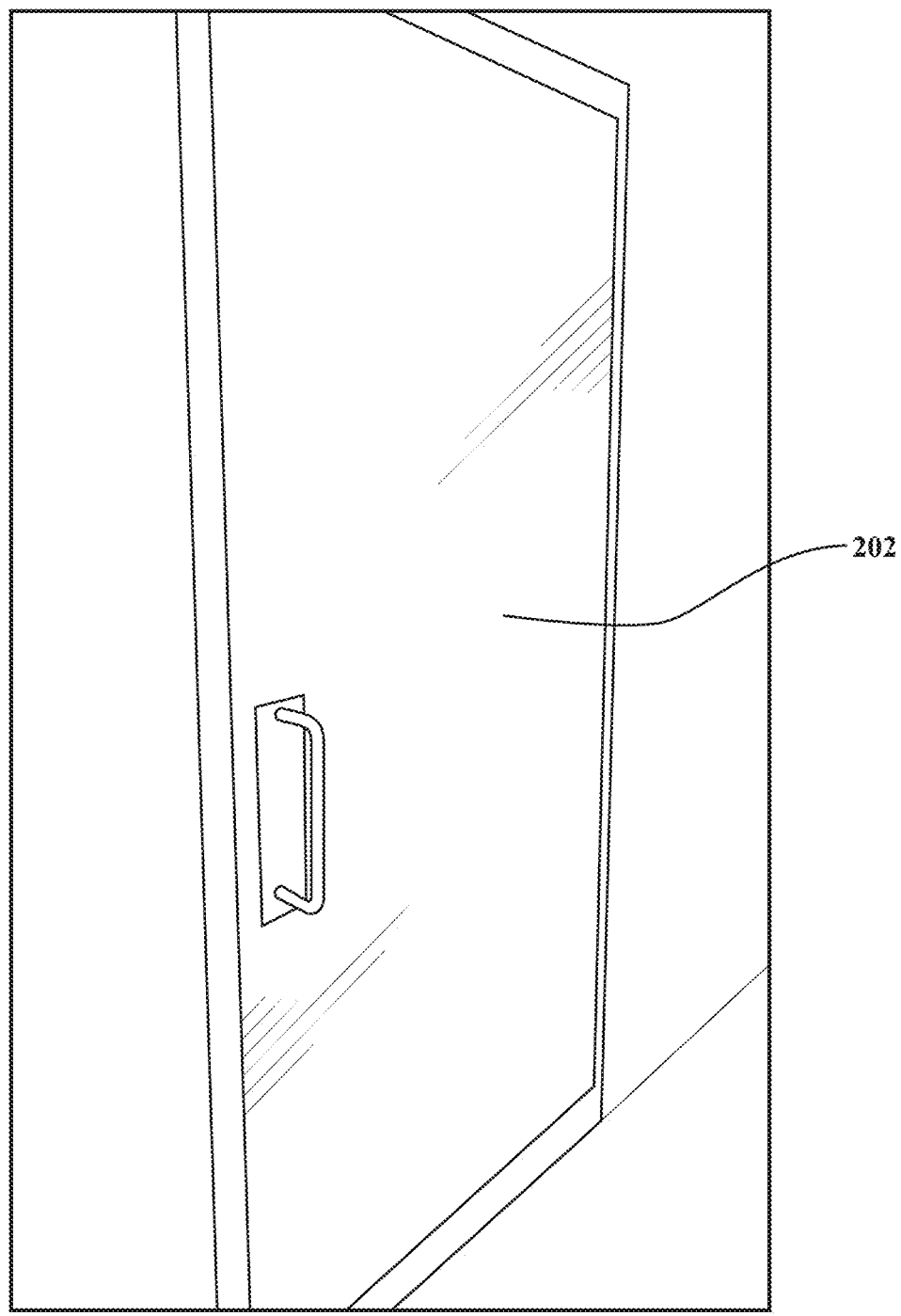
FIG. 3 is an example of an entrance for the medical services kiosk in which the techniques described may be practiced according to certain embodiments of the invention.
Figure 4:
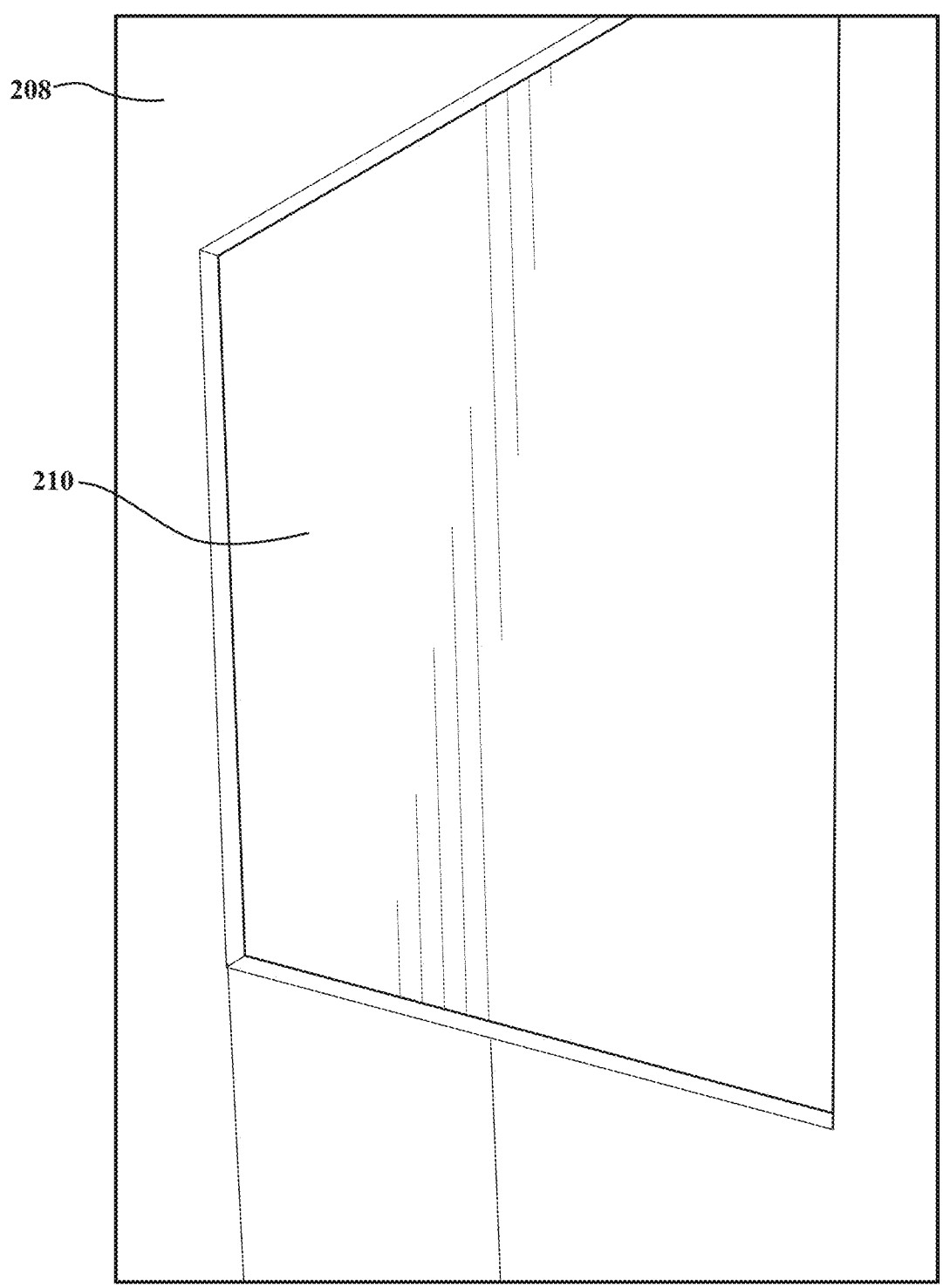
FIG. 4 is an example of an exterior surface of the medical services kiosk including a privacy screen window.

Referring to FIGS. 2-4, a medical services kiosk 200 is illustrated in accordance with an exemplary embodiment of the present invention, wherein the medical services kiosk 200 provides one or more of the aforementioned patient stations 110. As shown, the medical services kiosk 200 comprises a leftmost kiosk entrance 202, a rightmost entrance 204, a medical services system kiosk inventory storage component 206, an exterior window opening 208, and a privacy window panel 210. In one embodiment, the privacy window panel 210 may be configured to manually or automatically be set to an opaque mode preventing anyone from seeing into the patient station 110 from the exterior of the medical services kiosk 200.

Referring to FIGS. 2-14, in one embodiment, the medical services kiosk 200 includes one or more patient stations 110 comprising one or more individualized interior chambers 300, each of which provides the patient station 110 and is configured to each support a private and secure session between the patient 114 and the medical professional 124 via the patient client device 112 and the medical facility clinician device 122, respectively. In one embodiment, the medical services kiosk 200 comprises a plurality of entrances, doorways, or passages arranged throughout the exterior of the medical services kiosk 200 configured to automatically lock via a privacy-based automated locking mechanism securing the patient 114 in the interior chamber 300 while the patient 114 is in session with the medical professional 124 and automatically unlock when the session is completed. For example, the leftmost and rightmost entrances 202 and 204 may include automatic locks and an automatic glass shading element for providing privacy to a patient using the respective patient station 110 in each respective interior chamber 300.

Figure 13A:
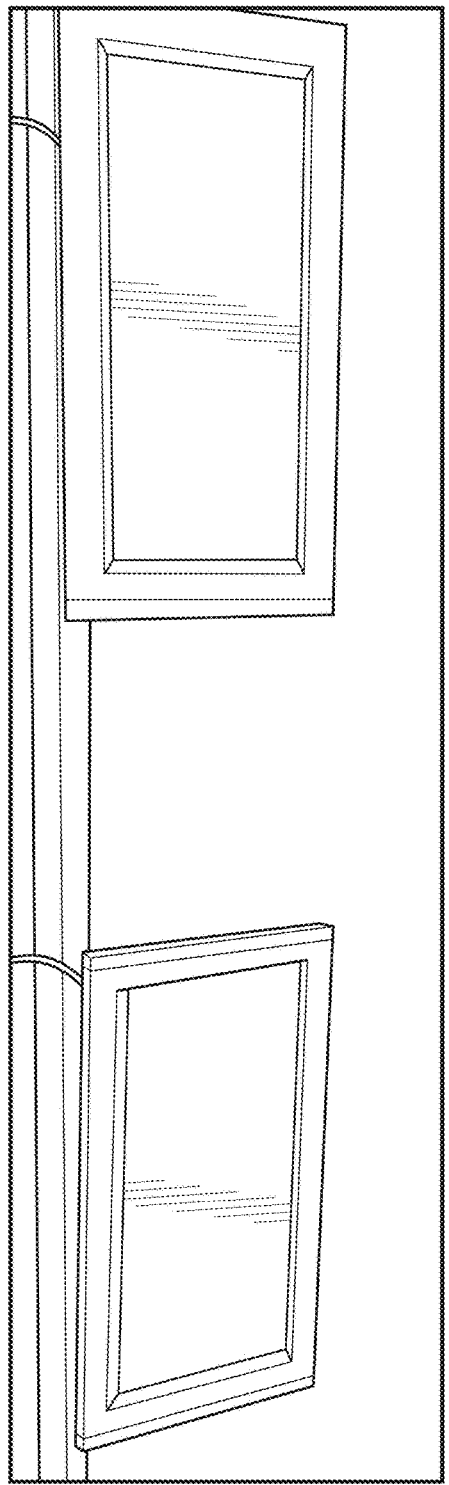
FIG. 13 is an example of the interior space of the medical services kiosk including a mono directional speaker and a white noise speaker.
Figure 13B:
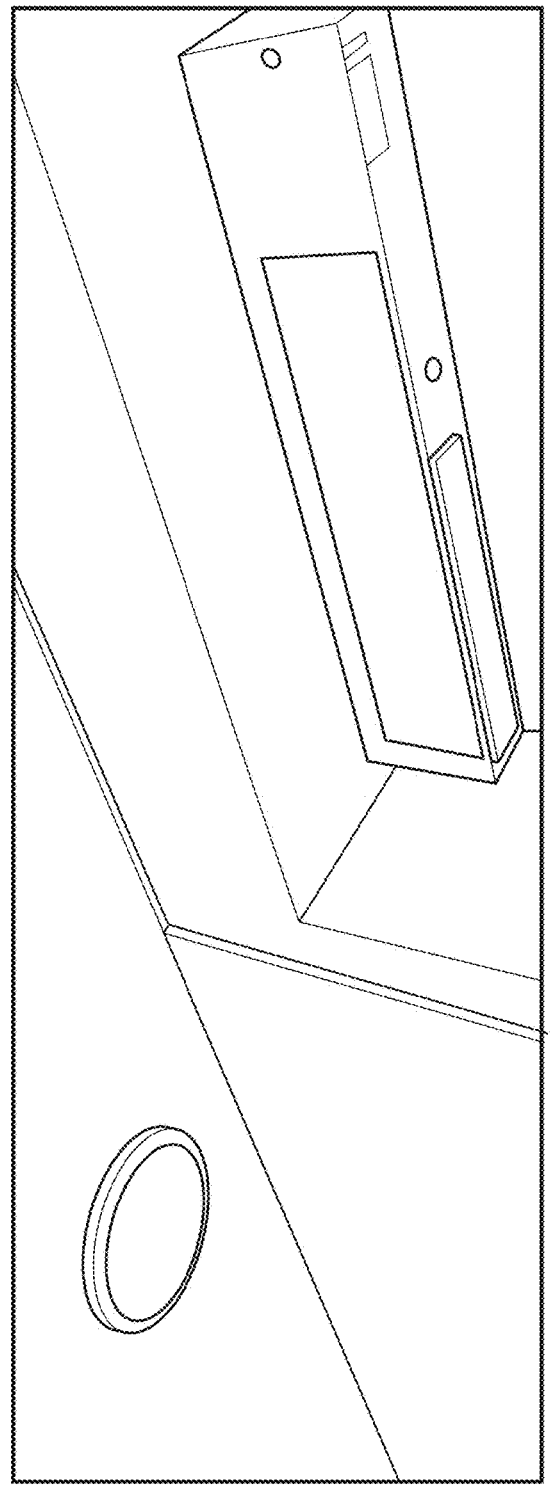
Figure 14:
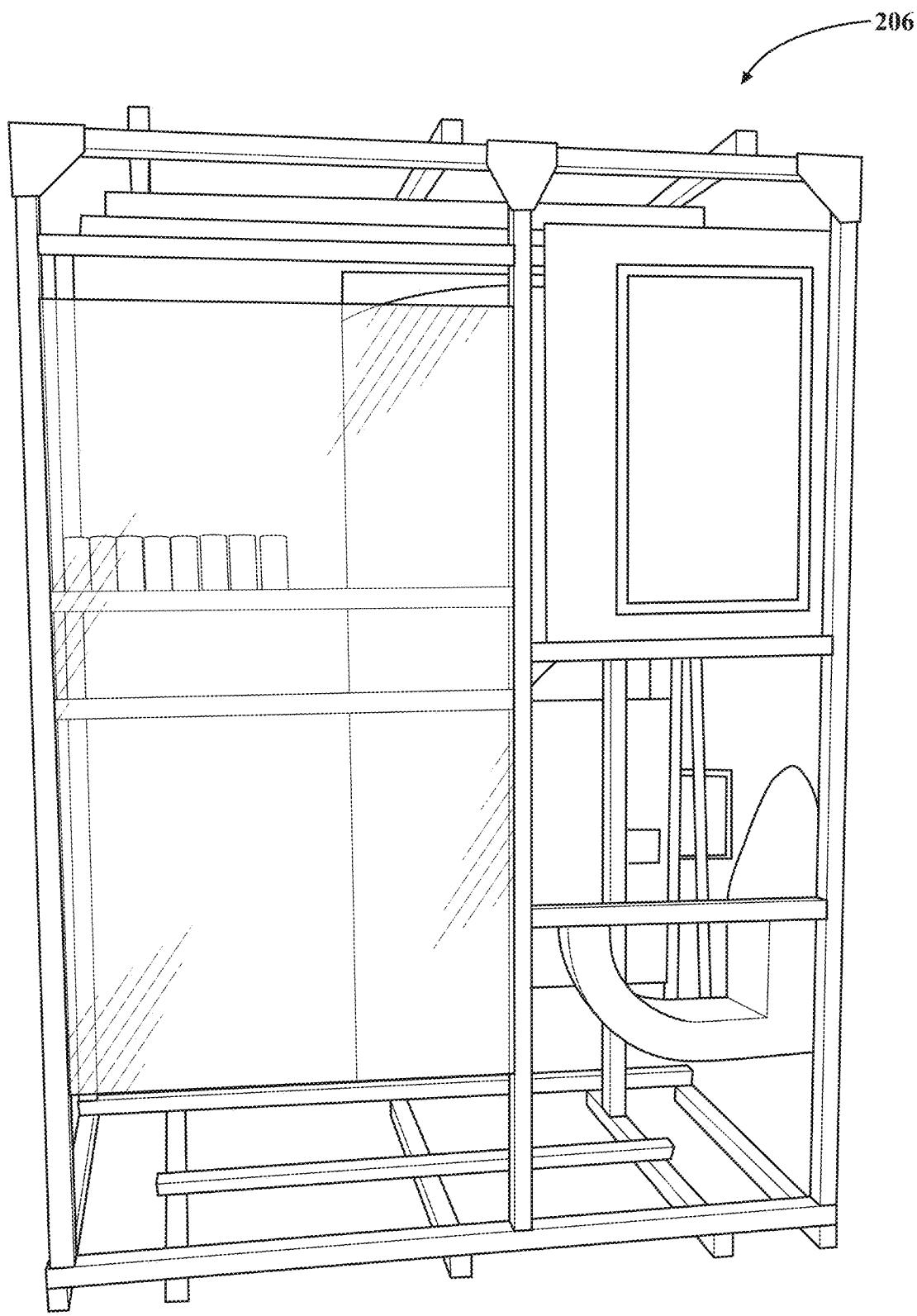
FIG. 14 is an example of an inventory storage chamber within the medical services kiosk in which the techniques described may be practiced according to certain embodiments of the invention.

In one embodiment, the medical services system kiosk inventory storage component 206 comprises a plurality of securely locked medicines and medical equipment configured to be distributed to the patient 114 in the interior chamber 300 upon a set of instructions administered by the medical professional 124 via the medical facility clinician device 122. The medical services system kiosk inventory storage component 206 may be configured to perform security checks via barcode, RFID, and/or a retractable camera device 304 in order for the medical professional 124 to verify the dispensed medicine, the patient 114 and/or effectively distribute valid prescriptions. In one embodiment, the medical services kiosk 200 comprises a plurality of airtight passageways to support transporting of the medicines and/or medical equipment from the medical services system kiosk inventory storage component 206 to the interior chamber 300, and provides noise attenuation, monodirectional technology, privatization mechanisms associated with the privacy window panel 210 in order to provide the patient 114 with maximum privacy, as shown in FIG. 13.

As best shown in FIGS. 5-13, in one embodiment, the interior chamber 300 includes the privacy window panel 210, a retractable camera device 304, a biometric/vitals measuring device 306, an arm support mechanism 308, a patient seating mechanism 310, a documentation receiving device 314, a user interaction panel 320, an ultra-violet sanitation system 324, an interior lighting mechanism 326, and an integrated scaling mechanism 330 comprising an outer flooring mechanism 332 and an inner flooring scaling mechanism 334. The interior chamber 300 may further comprise a plurality of retractable sensors, cameras, speakers, microphones, and other devices necessary for communication and transmittal of information from the patient station 110 to the remote medical facility 120. For example, the retractable camera device 304 may be configured to act as a sensor, camera, and microphone for monitoring and receiving bodily conditions while in the interior chamber 300 via thermal scanners, thermometers, and other mechanisms necessary to acquire useful bodily information from the patient 114. The privacy window panel 210 may be configured to function as a barrier wall between the plurality of interior chambers 300 within the medical services kiosk 200 or a privacy wall separating an interior chamber 300 from the exterior of the medical services kiosk 200. Privacy within each interior chamber 300 may also be provided by speakers emitting white noise throughout the interior chamber 300.

The interior chamber 300 may further include a monitor, screen, or projector configured to be mounted on any surface within the interior chamber 300 suitable for projecting an image of the medical professional 124 to the patient 114. In one embodiment, the user interaction panel 320, best shown in FIG. 8, comprises the projector, and may be an electrically operated telescopic column configured to be adjusted manually or automatically to the height or preferences of the patient 114. The projector may be configured to display an image of the remotely-located medical professional 124, optionally in combination with a background image allowing the medical professional 124 to be portrayed with a background image such as, but not limited to, the logo or other indicator associated with the remote medical facility 120 and/or the medical professional 124.

In operation, the patient 114 enters into one of the separated interior chambers 300 (FIG. 5) via one of the corresponding entrances 202 and 204 (FIG. 2) and may initiate a session on the patient station 110 by interacting with the user interaction panel 320 (FIG. 7) which may be communicatively coupled to or interchangeable with the patient client device 112 of the patient station 110. Upon interacting with the user interaction panel 320, the patient 114 is prompted with introductory questions and asked to provide information such as medical history, current medications, or any other relevant information necessary to assist the rendering of medical services. In one embodiment, information associated with the patient 114 may be linked and integrated from an outside data source via logging in an account if applicable. The patient 114 may be prompted for insurance information and a payment method if not already provided or already introduced or retrieved from the outside data source. In one embodiment, the documentation receiving device 314 may receive insurance information or other documents of the patient 114 by placing insurance documents or other information documents on the surface of the documentation receiving device 314 for scanning. Upon establishment of a valid session, the patient 114 may be prompted with a series of questions regarding the purpose of the session and further prompted for information that requires interaction with components within the interior chamber 300.

Figure 9:
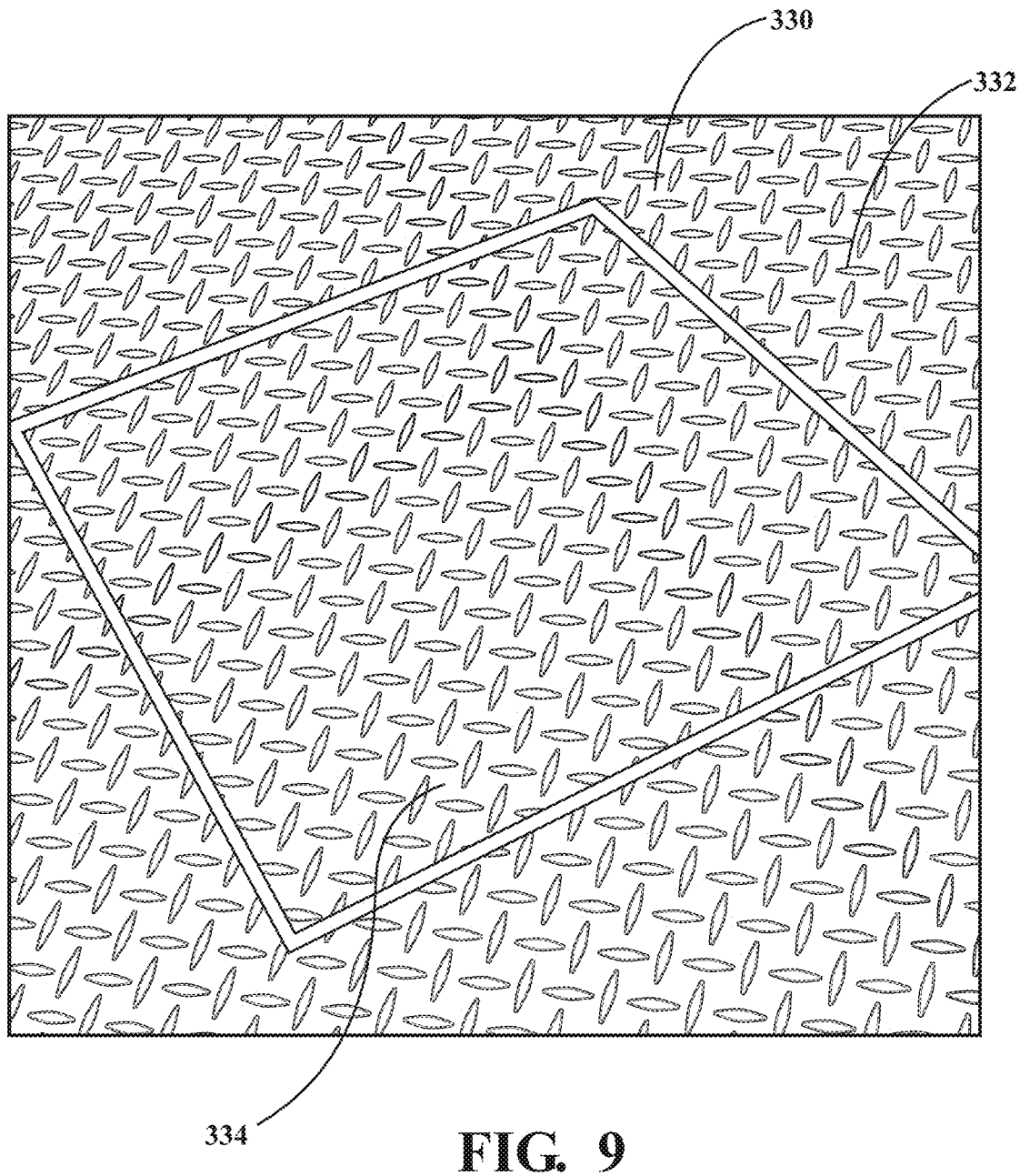
FIG. 9 is an example of an integrated scaling system within the interior of the medical services kiosk in which the techniques described may be practiced according to certain embodiments of the invention.
Figure 10:
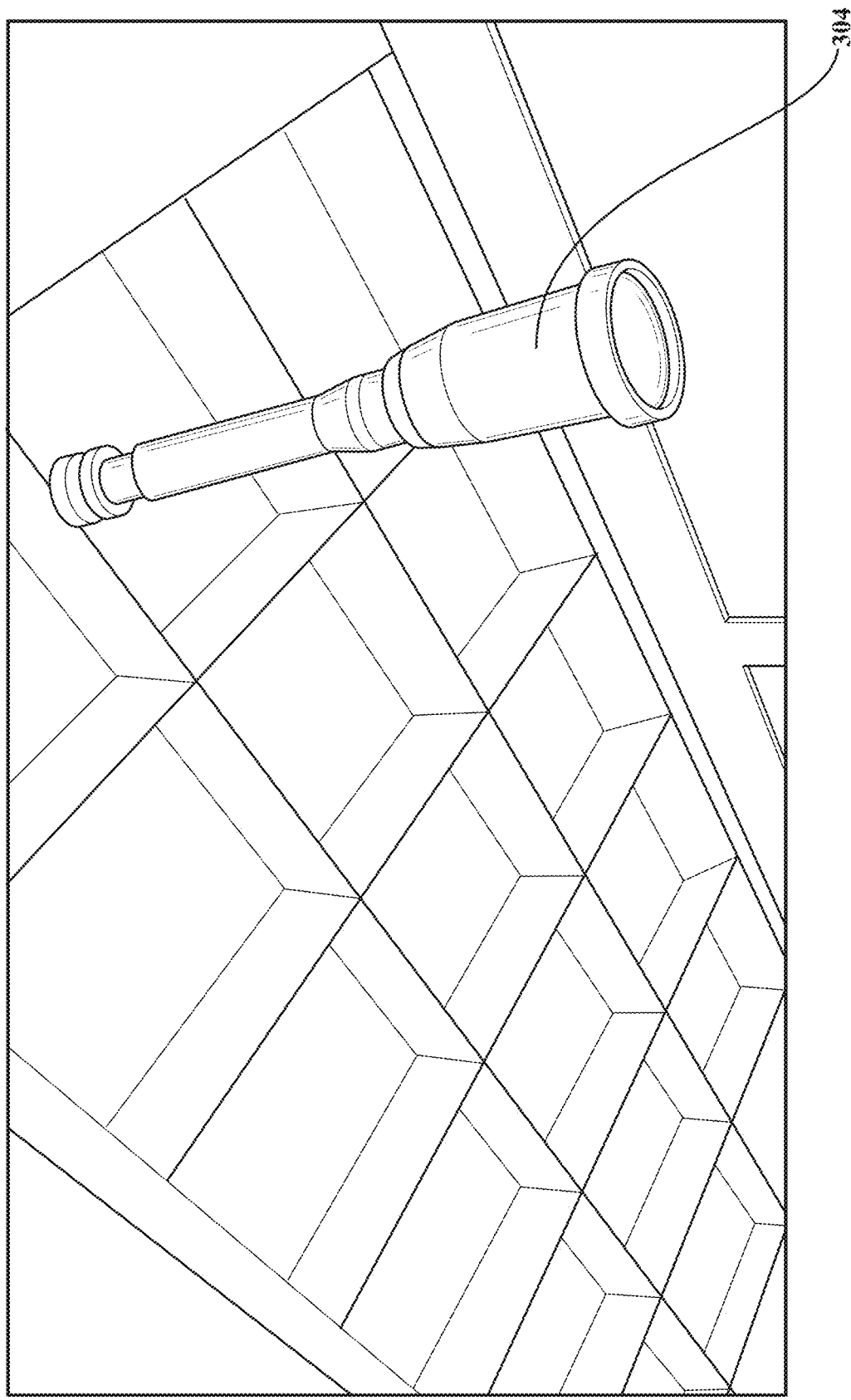
FIG. 10 is a second example of the ultraviolet-based sanitation system within the interior of the medical services kiosk comprising a retractable camera in which the techniques described may be practiced according to certain embodiments of the invention.

The interior chamber 300 is configured for the patient 114 to sit in the patient seating mechanism 310 (FIGS. 5 and 6) with their back aligned or supported by a surface of the interior chamber 300 and their arm housed by the arm support mechanism 308. The patient station 110 of the medical services system 100 may collect the weight of the patient 114 via prompting the patient to utilize the integrated scaling mechanism 330 by standing in the inner flooring scaling mechanism 334 which is best shown in FIG. 9. The inner flooring scaling mechanism 334 may include a calibrated scale, plurality of measurement sensors, or any other means suitable for obtaining an accurate weight and/or height of the patient 114, and the outer flooring mechanism 332 may be integrated with the remainder of flooring within the interior chamber 300. The integrated scaling mechanism 330 is not limited to application within the medical services system 100.

Figure 5:
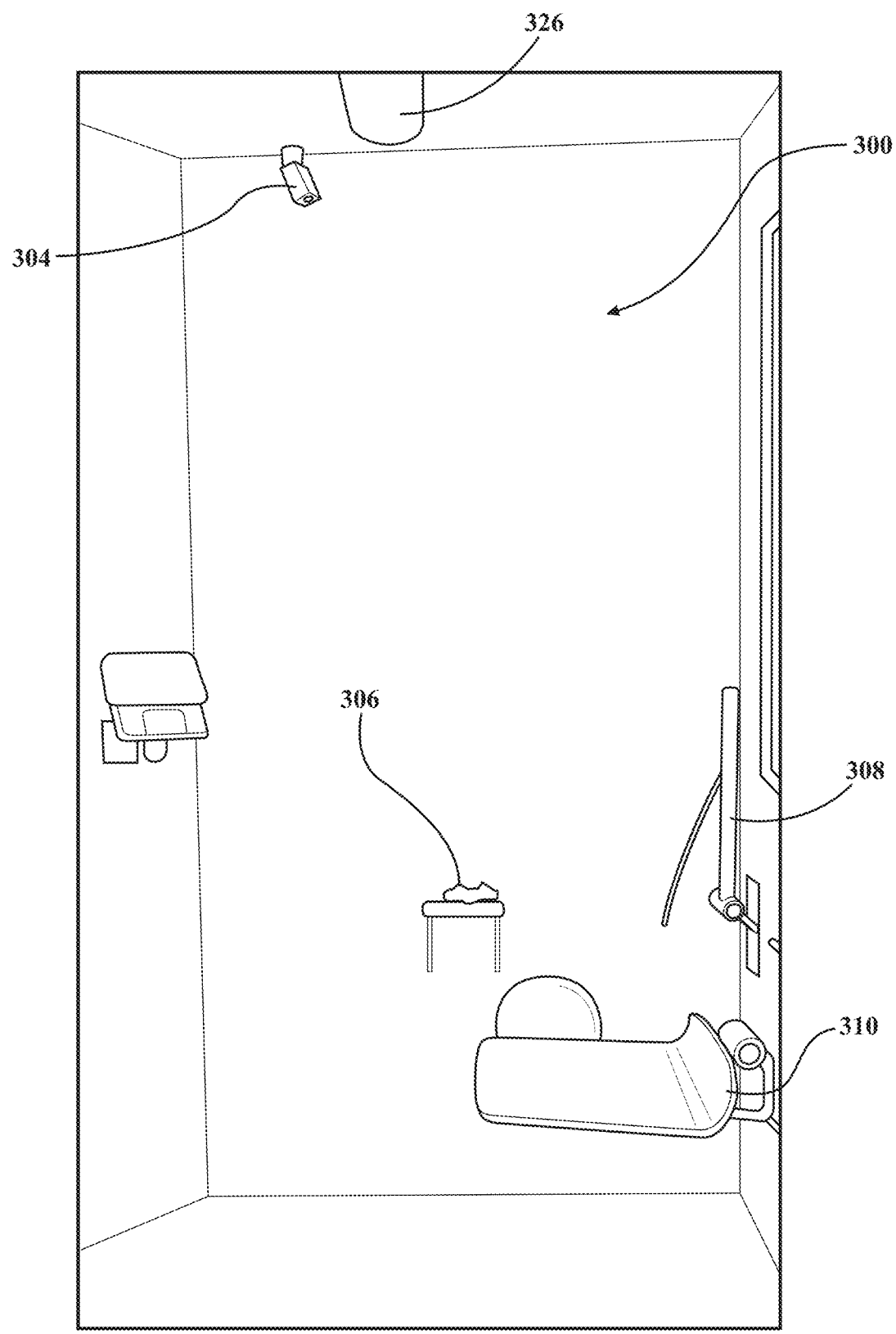
FIG. 5 is an example of an interior space of the medical services kiosk in which the techniques described may be practiced according to certain embodiment of the inventions.
Figure 6:
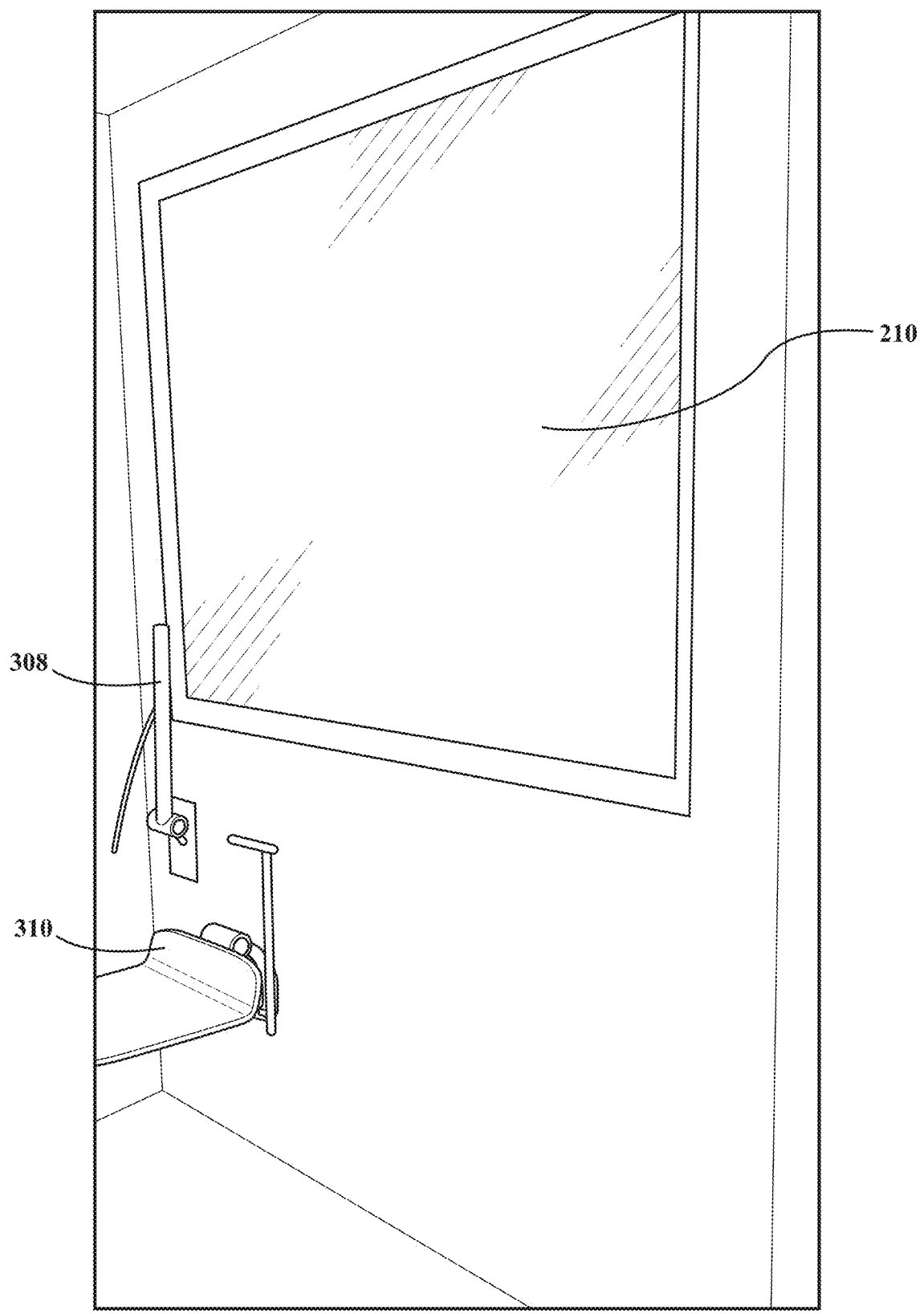
FIG. 6 is an example of the interior space of the medical services kiosk including the privacy screen window.
Figure 7:
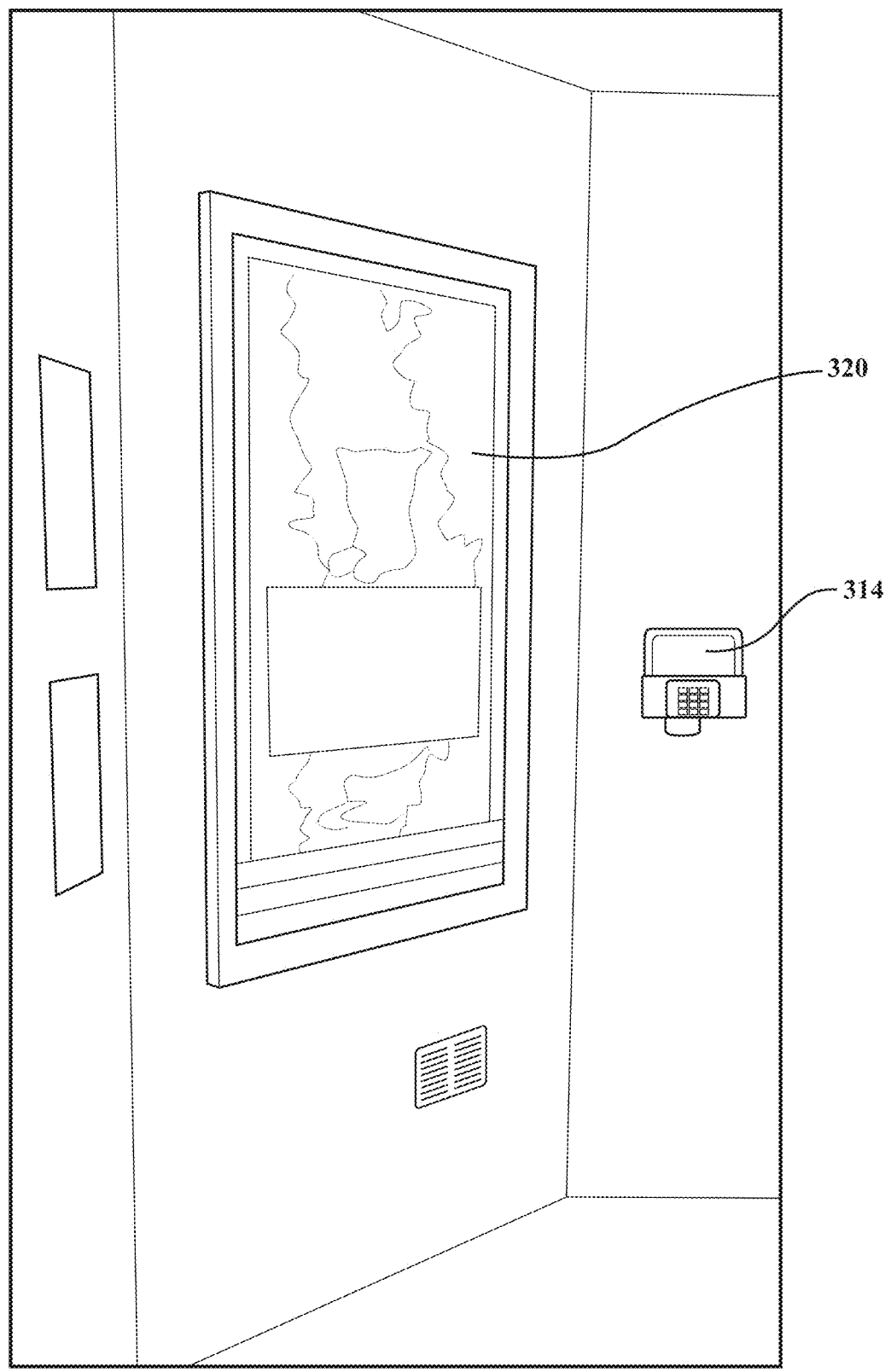
FIG. 7 is an example of the interior space of the medical services kiosk including an interactive user interface.
Figure 11:
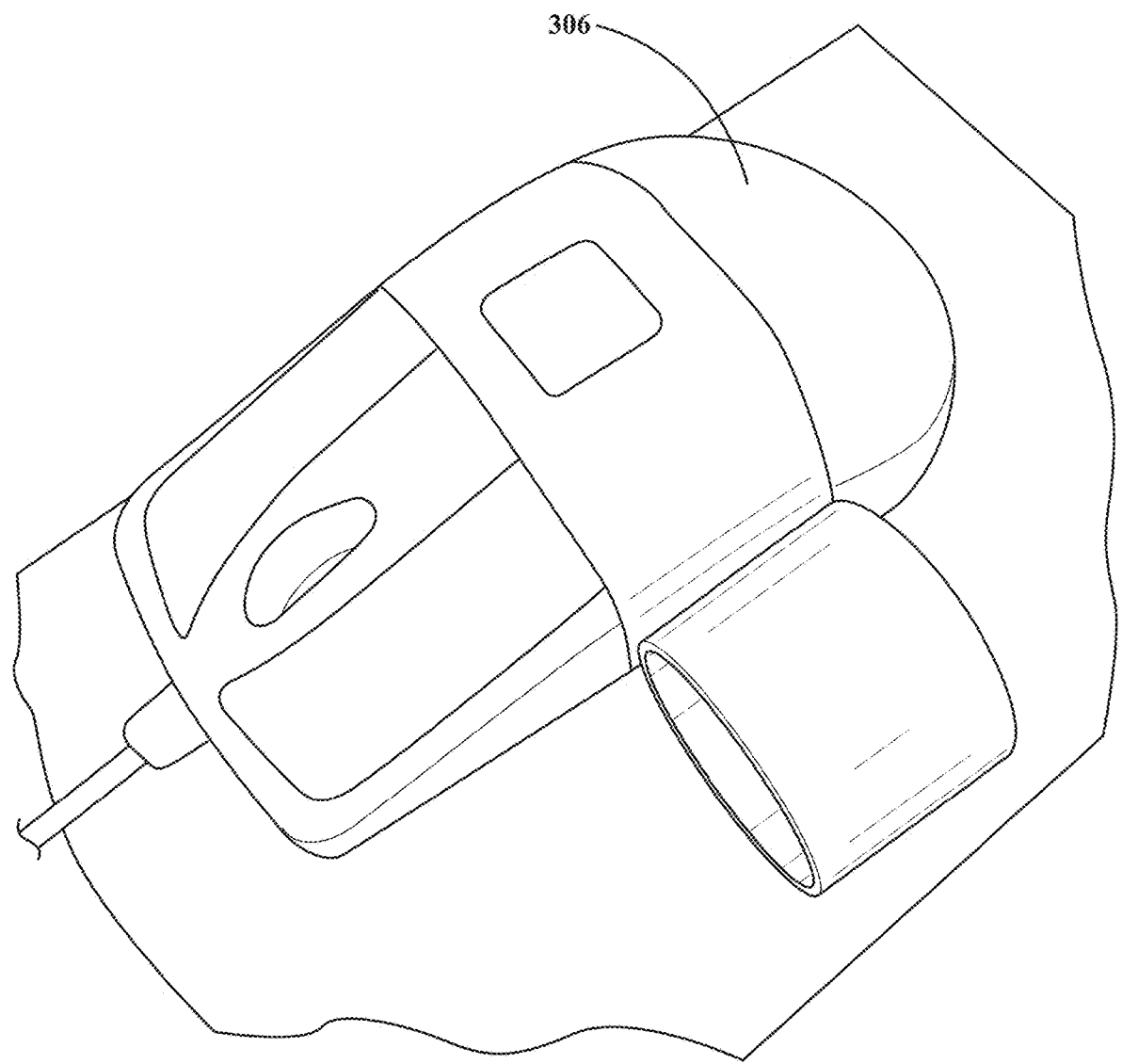
FIG. 11 is an example of a biometric/vitals measuring device within the interior of the medical services kiosk in which the techniques described may be practiced according to certain embodiments of the invention.
Figure 12:
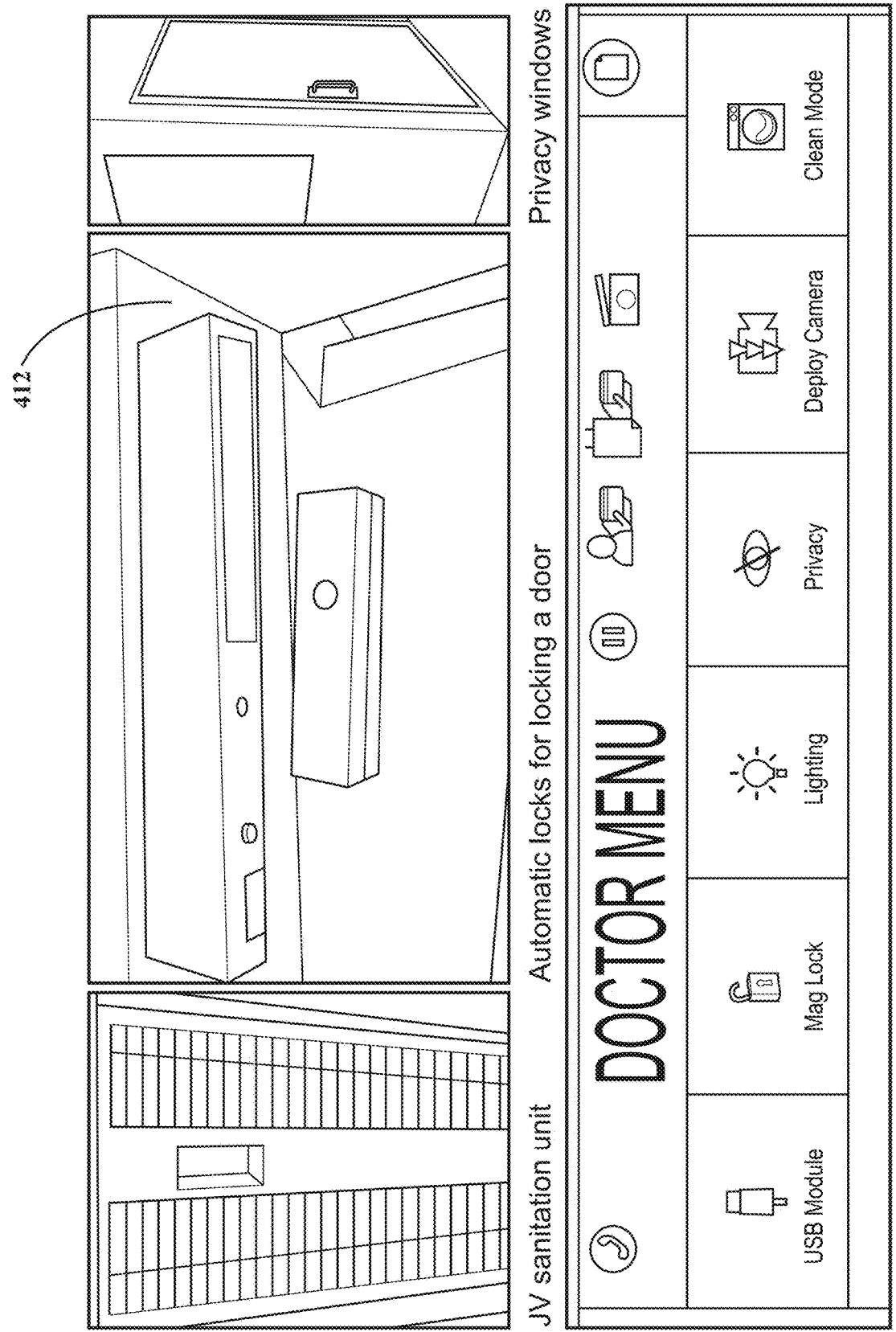
FIG. 12 is an example of an interactive user interface associated with a remote medical facility configured to control components within the interior of the medical services kiosk in which the techniques described may be practiced according to certain embodiments of the invention.

In one embodiment, while the arm is housed in the arm support mechanism 308 as shown in FIG. 5, the patient 114 is able to provide their biometrics and body vitals via the biometric/vitals measuring device 306, which is best shown in FIG. 11. The biometric/vitals measuring device 306 may comprise sensors, blood pressure monitoring technology, and any other relative medical technology suitable for acquiring vital signs of the patient 114. In one embodiment, the biometric/vitals measuring device 306 further includes an adjustable bracelet-like mechanism comprising a cavity suited for adjustable fitting to the wrist of the patient 114.

Figure 8:
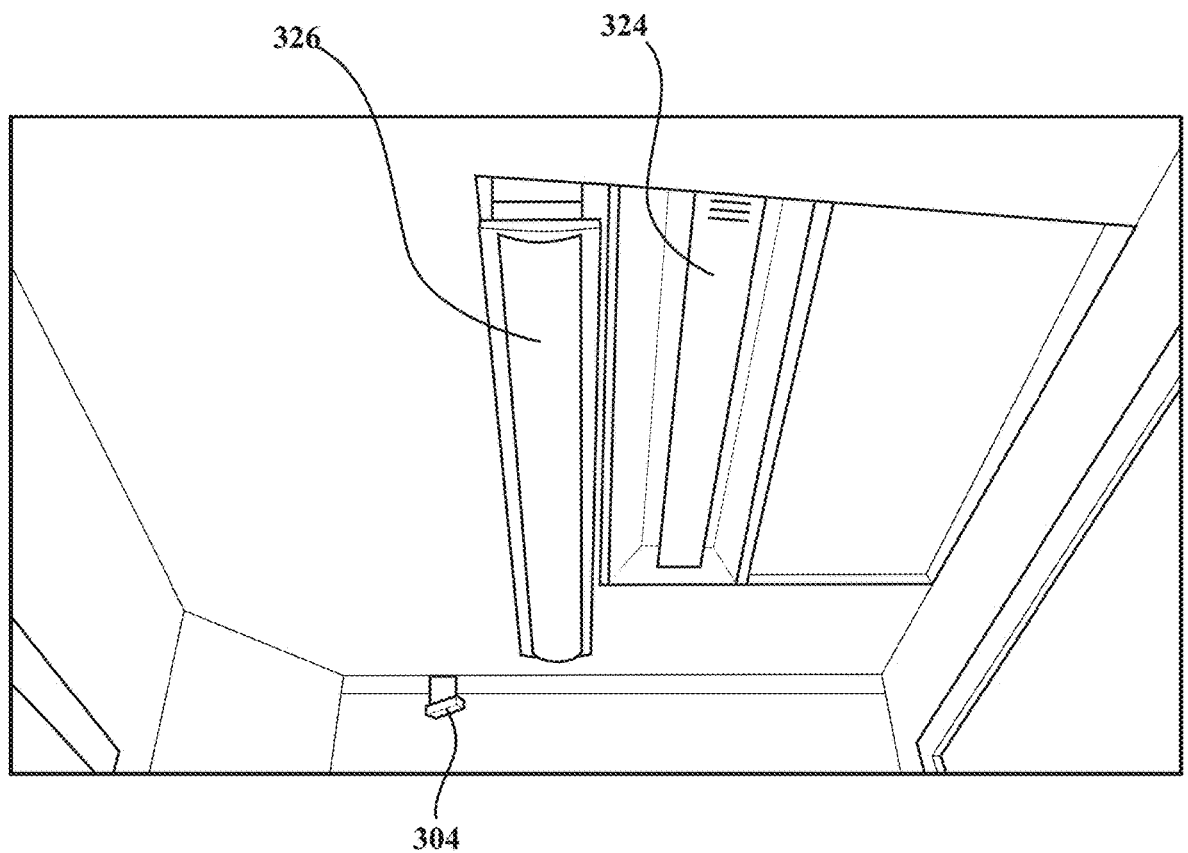
FIG. 8 is a first example of an ultraviolet-based sanitation system within the interior of the medical services kiosk in which the techniques described may be practiced according to certain embodiments of the invention.

As shown in FIG. 8, in one embodiment, the interior chamber 300 comprises the ultra-violet sanitation system 324 within the ceiling area, and the ultra-violet sanitation system 324 and the interior lighting mechanism 326 may be integrated into one unit within the ceiling area. The ultra-violet sanitation system 324 may be communicatively coupled to the privacy-based automated locking mechanism, which may both be controlled by the remote medical facility 120. The ultra-violet sanitation system 324 is configured to sterilize or sanitize organic and inorganic matter within the interior chamber 300 via a combination of ultraviolet light and ultrasound waves. The ultra-violet sanitation system 324 may be engaged or activated after termination of a session when the patient 114 exits the interior chamber 300 or periodically upon lack of detection of a person within the interior chamber 300.

Referring to FIGS. 15-26, a remote medical facility space 400 is illustrated in accordance with an exemplary embodiment of the present invention. As shown, the remote medical facility space 400 comprises the medical facility clinician device 122, associated with the medical professional 124, affixed to a remote medical facility client device stand 402, an adjustable platform 404 comprising a first user indicator component 406 and a second user indicator component, a monitor 410, the floating camera component 420, a remote medical facility interactive interface 412, and a remote medical facility control unit 414, which may be a LED Controller. In some embodiments, the medical facility clinician device 122 is configured to be detachable from the remote medical facility client device stand 402. In one embodiment, the remote medical facility client device stand 402 and the adjustable platform 404 are configured to be manually or automatically adjusted to the height or preferences of the medical professional 124, and the floating camera component 420 may comprise a plurality of sensors, image processing units, or microphones necessary in order to support live interaction with the patient 114.

Figure 15:
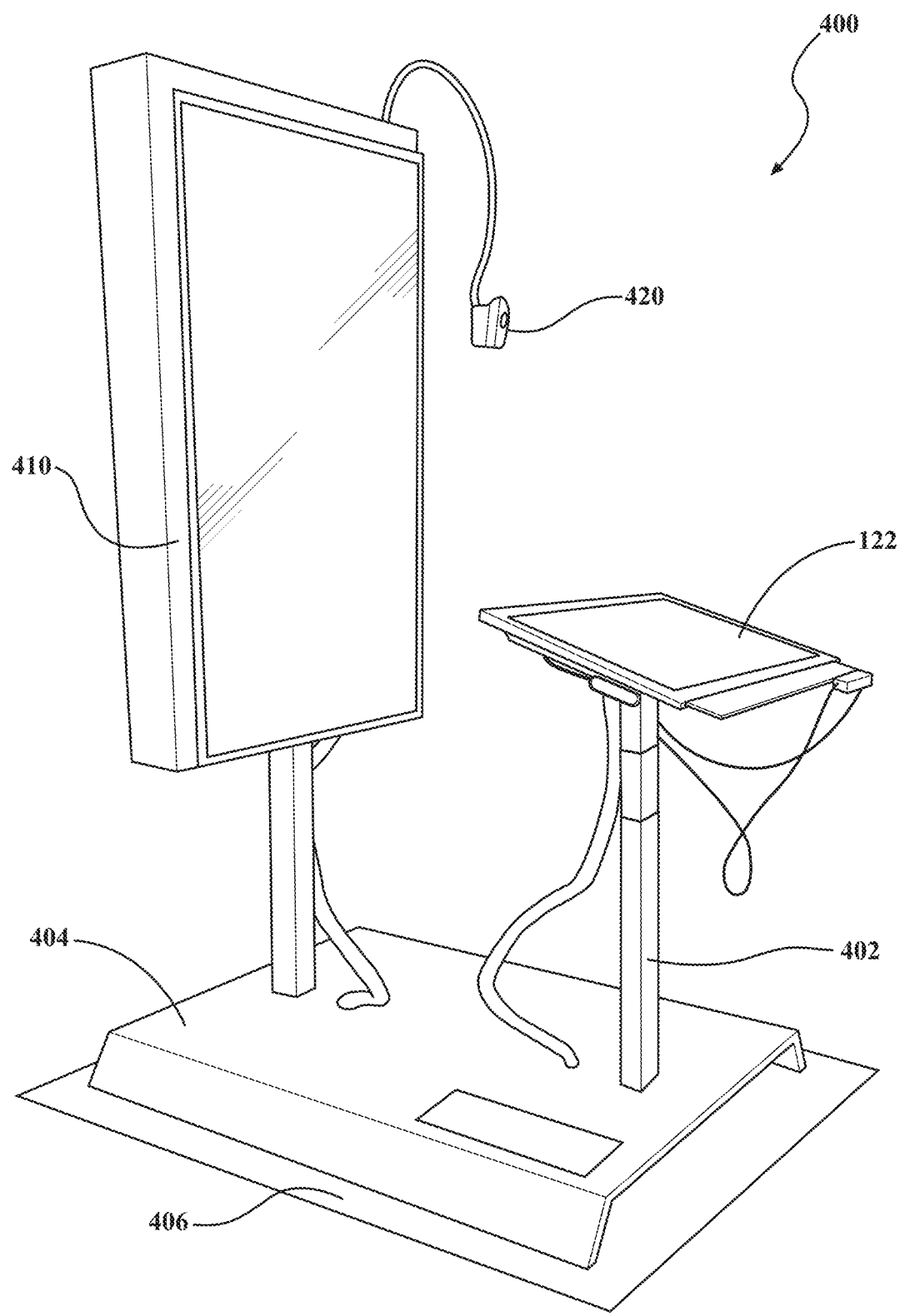
FIG. 15 is a left front-side view of an example of a space of a remote medical facility of the medical services kiosk in which the techniques described may be practiced according to certain embodiments of the invention.
Figure 16:
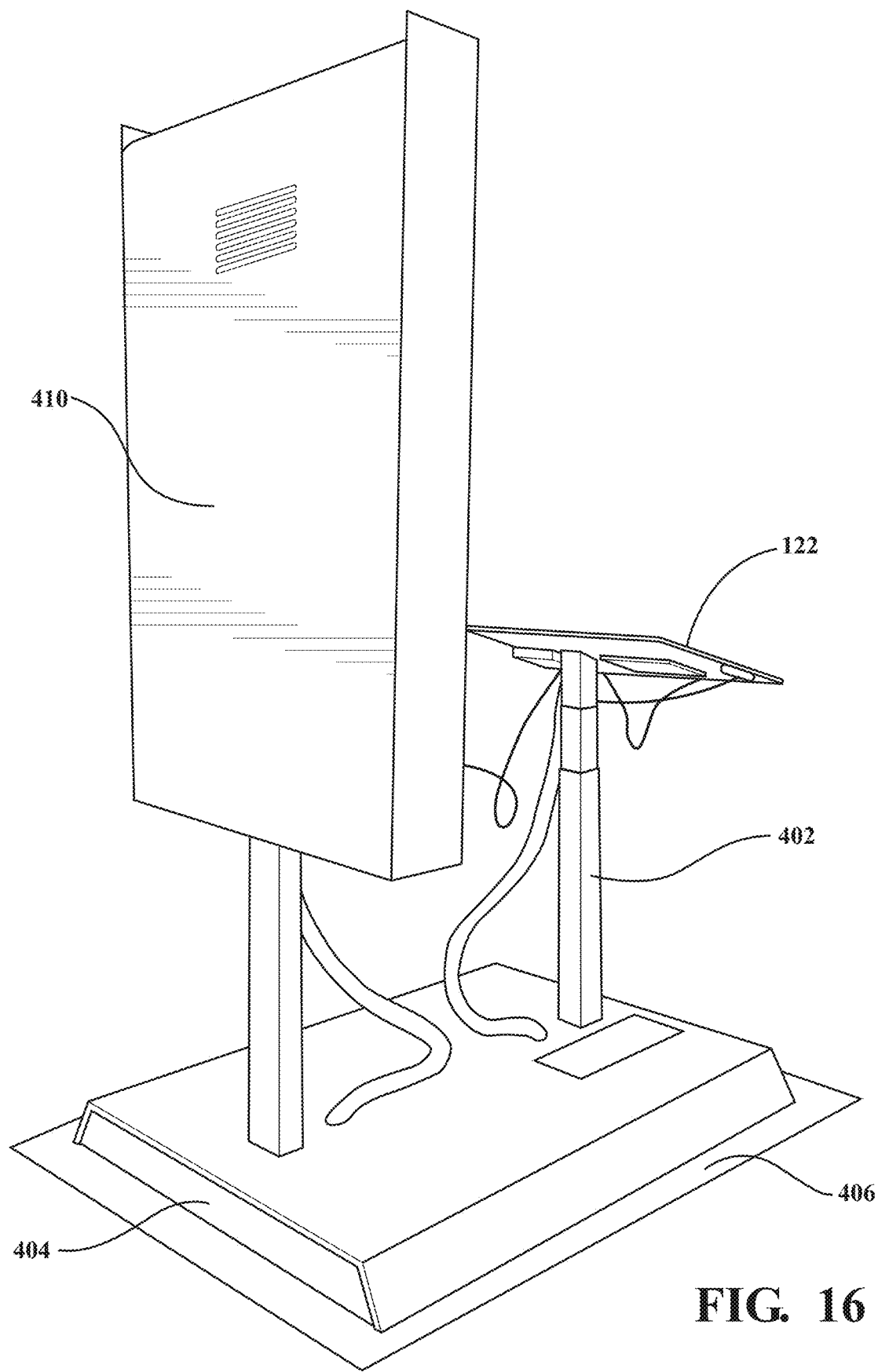
FIG. 16 is a left rear-side view thereof.
Figure 17:
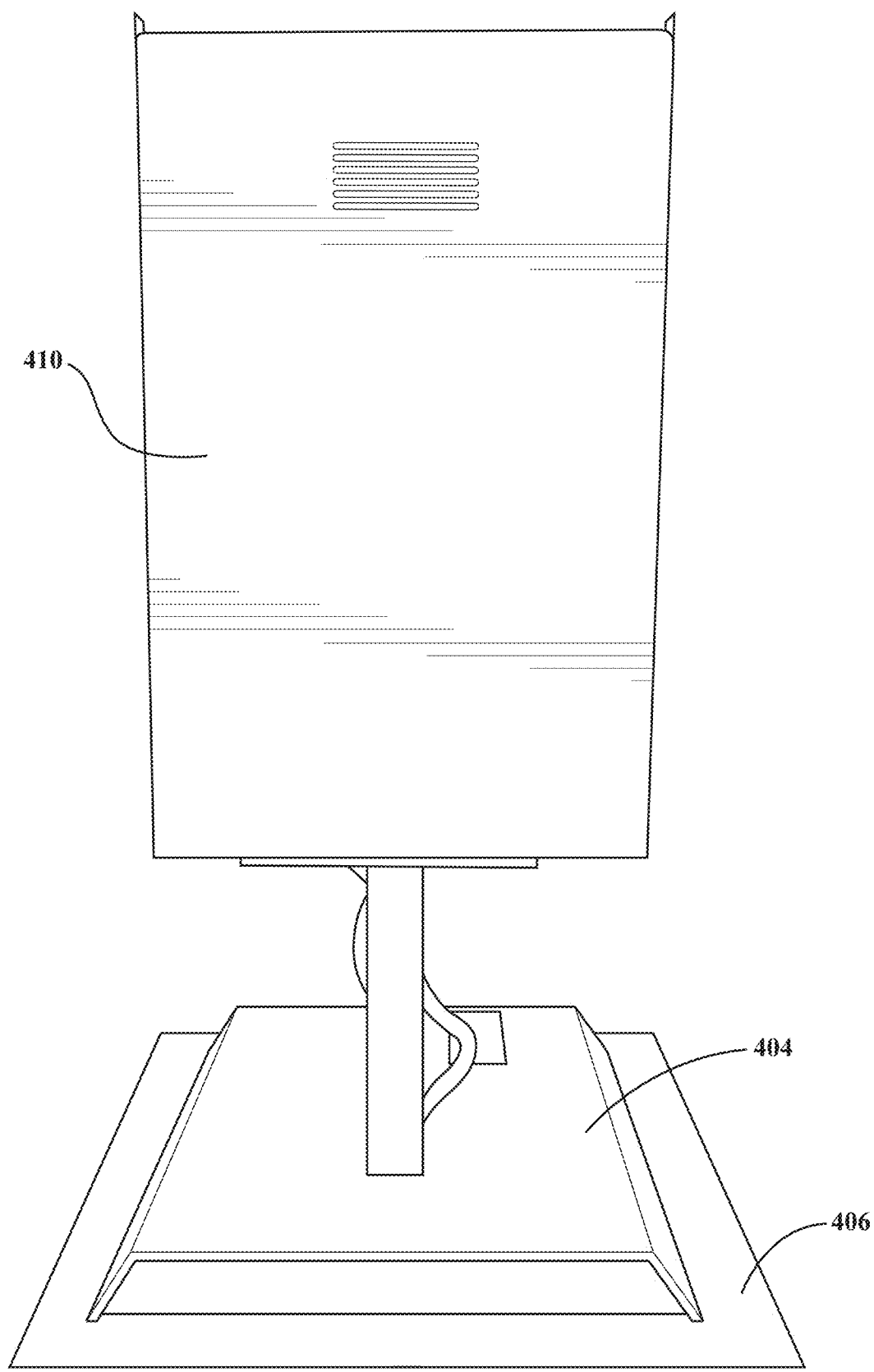
FIG. 17 is a back view thereof.
Figure 18:
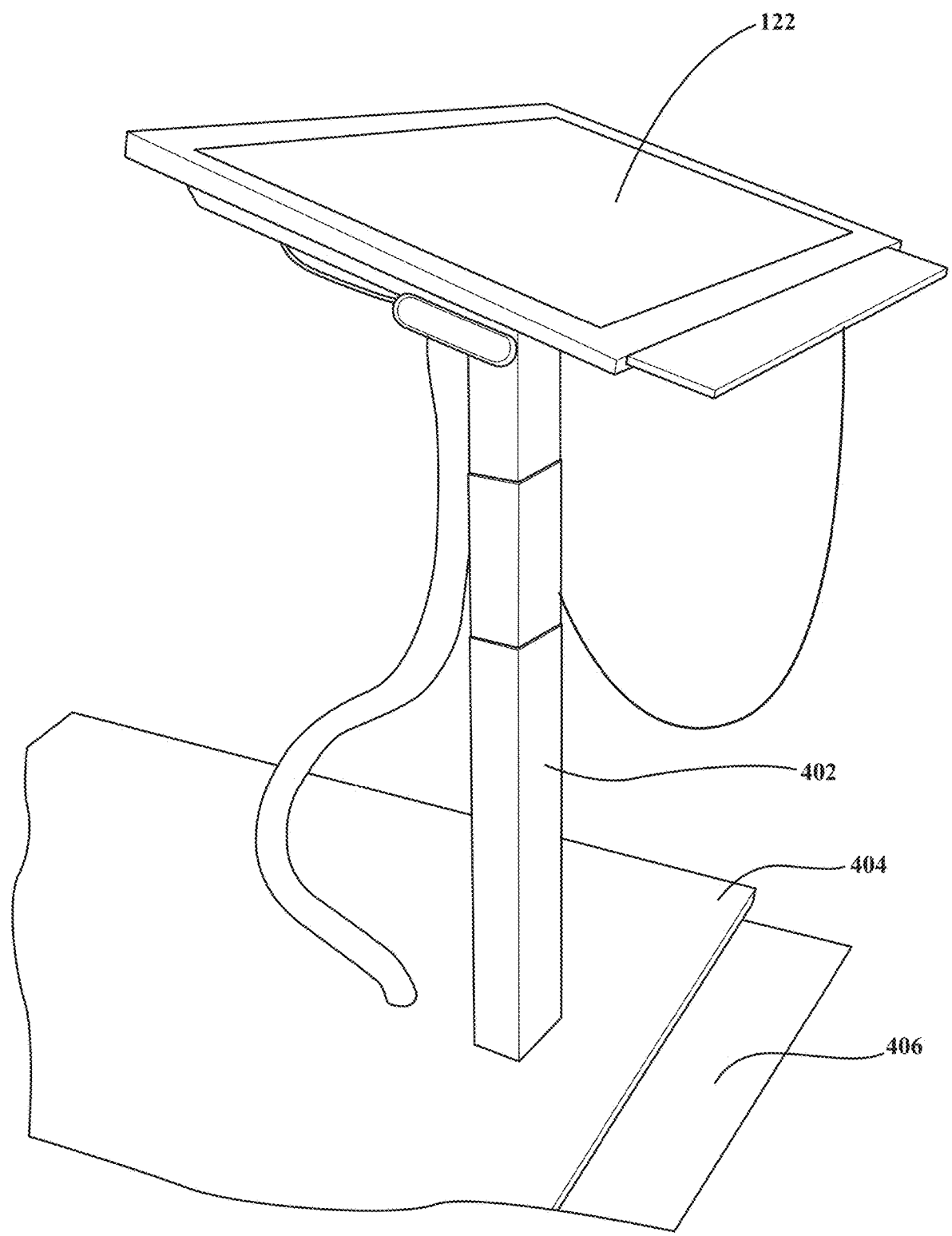
FIG. 18 is a left side view of a client device within the space of the remote medical facility of the medical services system in which the techniques described may be practiced according to certain embodiments of the invention.
Figure 19:
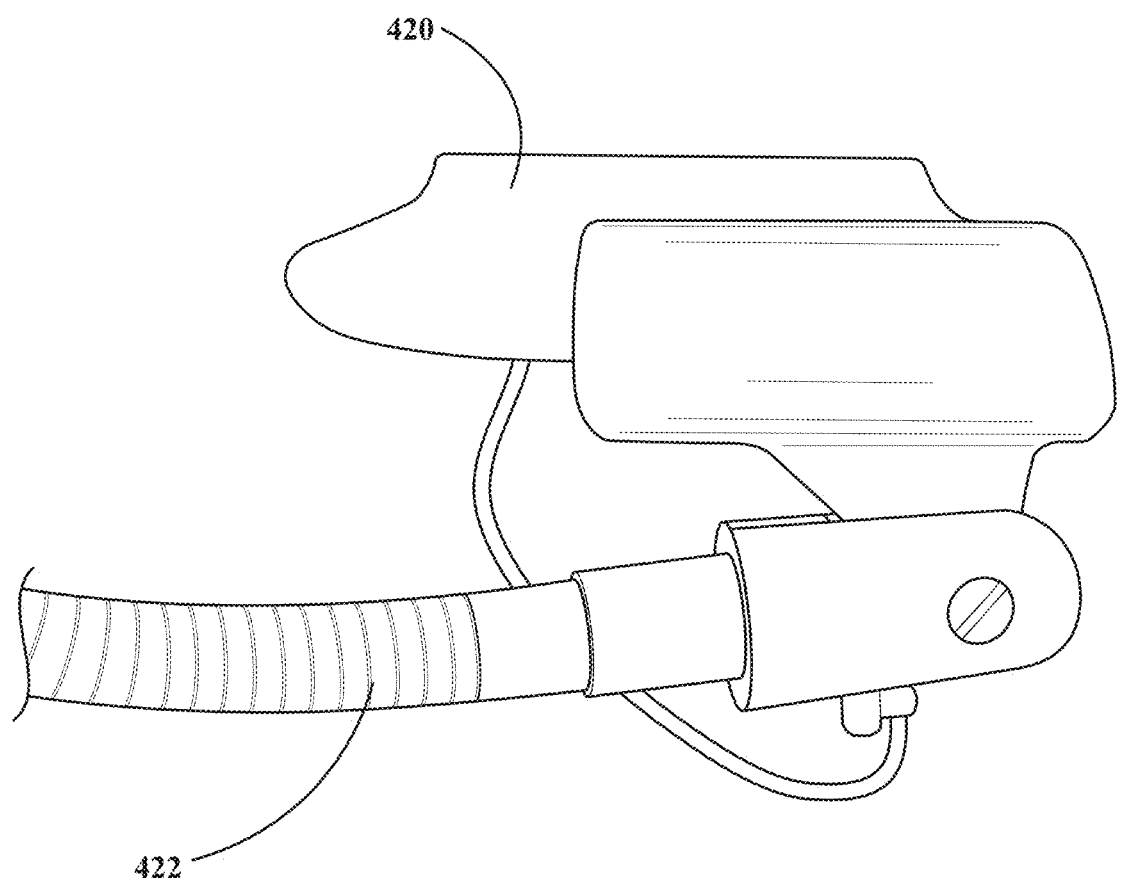
FIG. 19 is a first example of a floating camera within the space of the remote medical facility of the medical services system in which the techniques described may be practiced according to certain embodiments of the invention.
Figure 20:
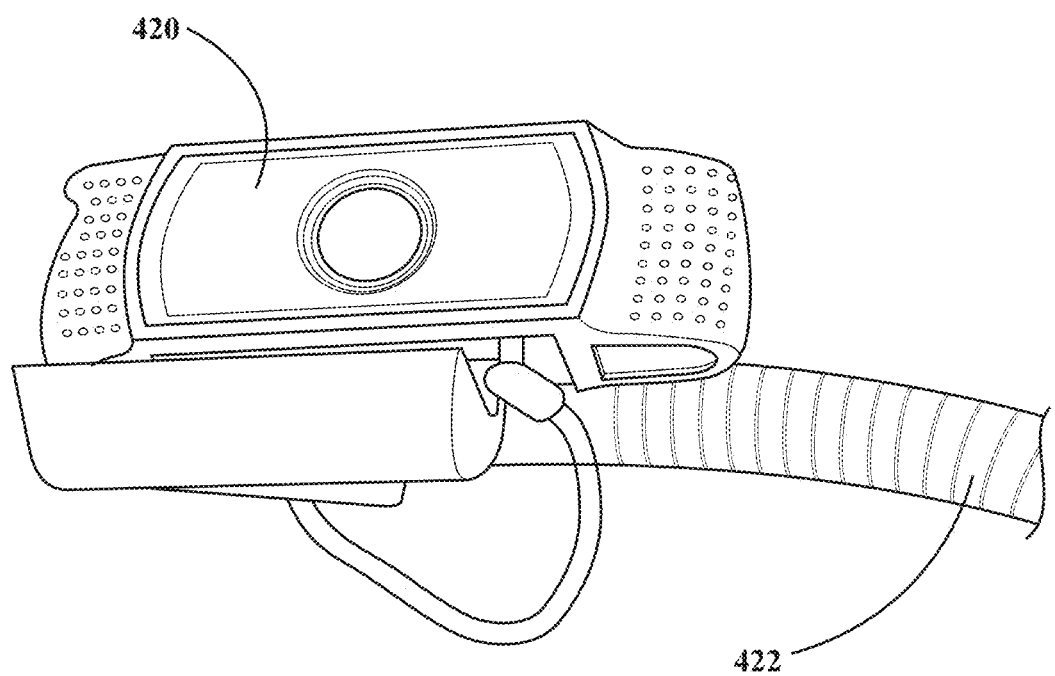
FIG. 20 is a second example of a floating camera within the space of the remote medical facility of the medical services system in which the techniques described may be practiced according to certain embodiments of the invention.
Figure 21:
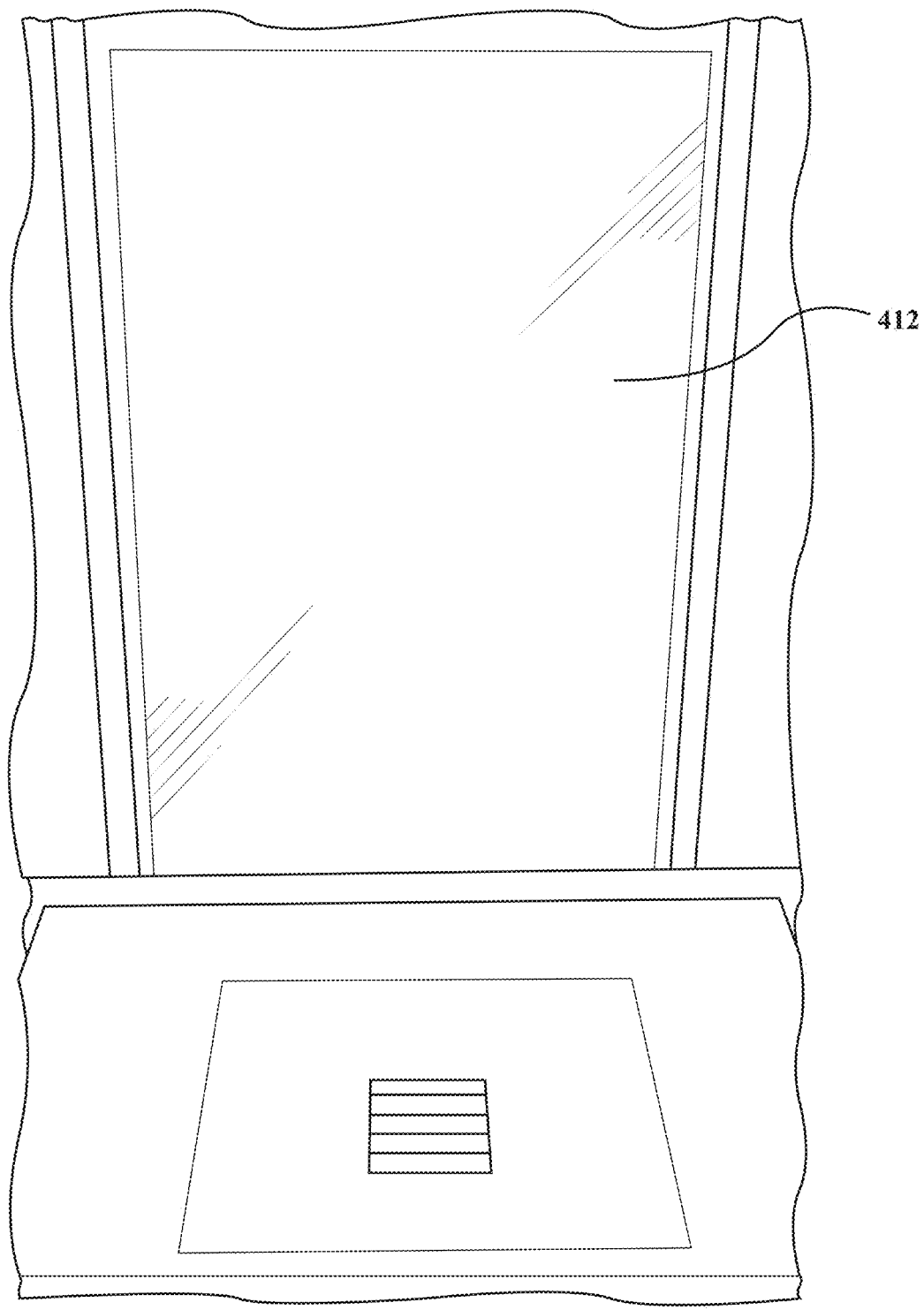
FIG. 21 is an example of a graphical user interface depicted on an interactive interface within a remote medical facility of the medical services system in which the techniques described may be practiced according to certain embodiments of the invention.
Figure 22:
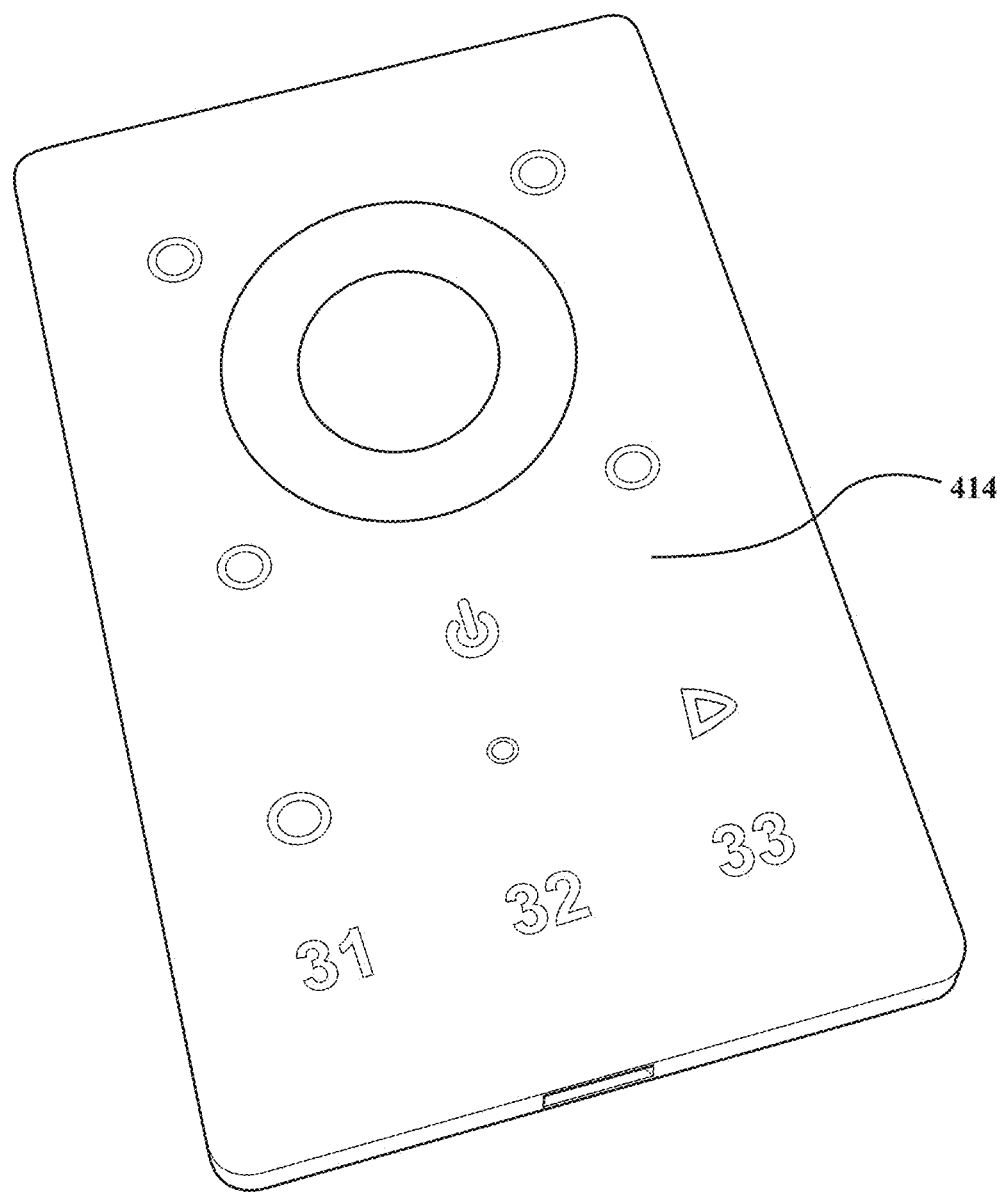
FIG. 22 is an example of a LED controller within a remote medical facility of the medical services system in which the techniques described may be practiced according to certain embodiments of the invention.
Figure 23:
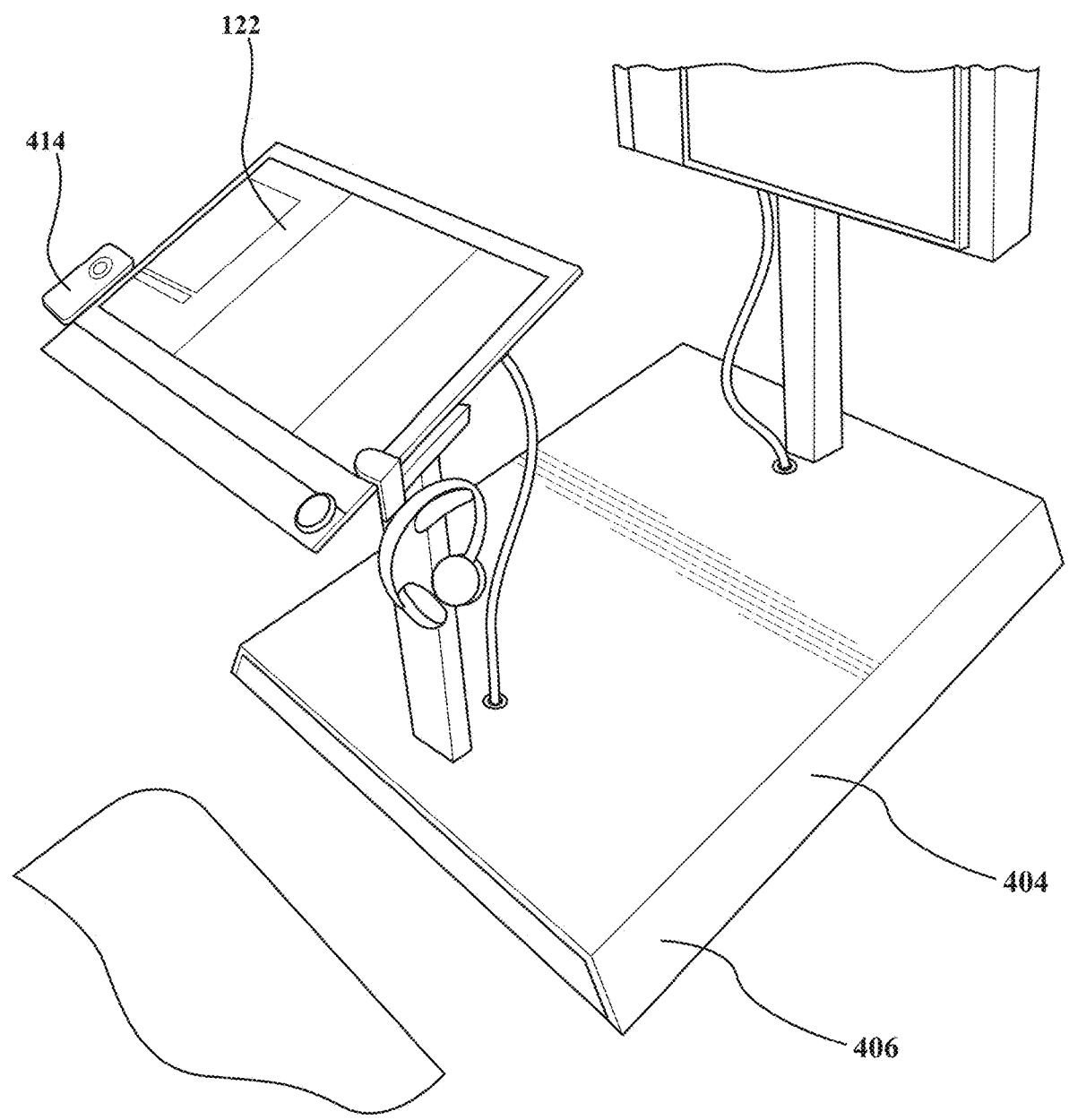
FIG. 23 is a right front-side view of an example of a client device on a platform within the remote medical facility of the medical services kiosk in which the techniques described may be practiced according to certain embodiments of the invention.
Figure 24:
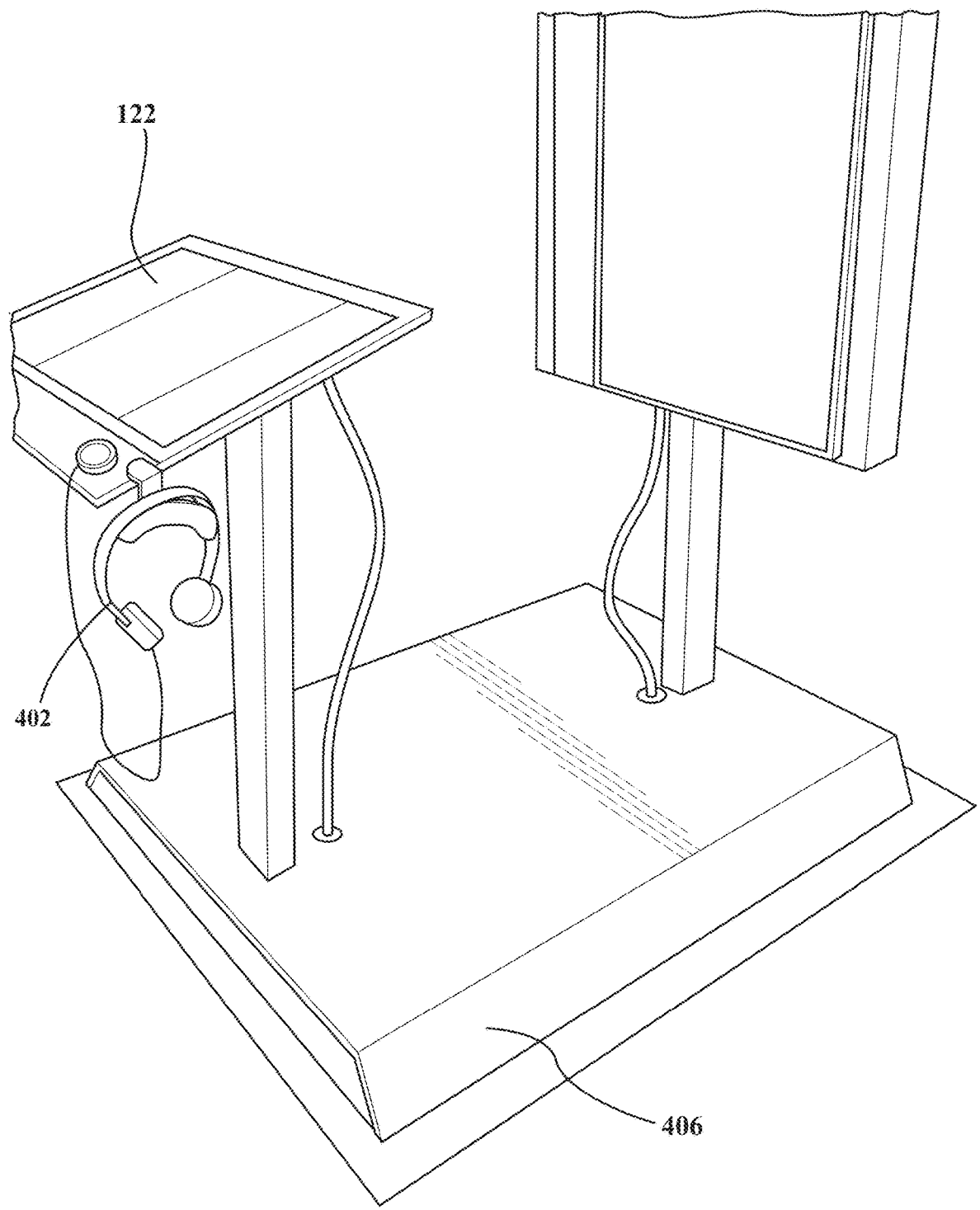
FIG. 24 is a right front-side view of an example of the space within the remote medical facility of the medical services kiosk in which the techniques described may be practiced according to certain embodiments of the invention.
Figure 25:
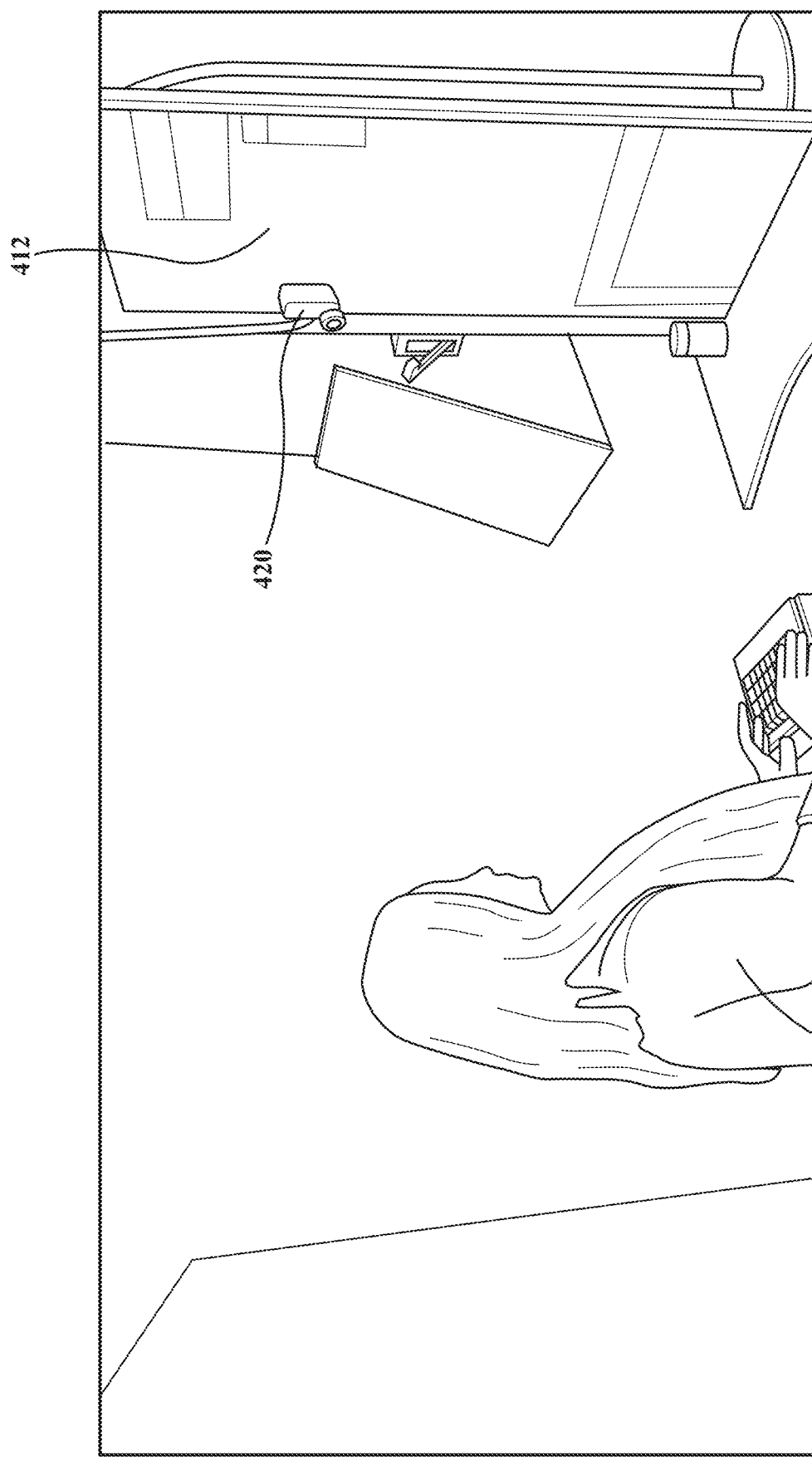
FIG. 25 is a first example of a medical professional in the space within the remote medical facility of the medical services kiosk in which the techniques described may be practiced according to certain embodiments of the invention.

In one embodiment, the remote medical facility space 400 comprises the floating camera component 420 affixed to a gooseneck support mechanism 422. The floating camera component 420 may be affixed to the remote medical facility interactive interface 412 via the gooseneck support mechanism 422 acting as an adjustable and extendable arm, as shown in FIG. 15. The floating camera component 420 may be configured to be positioned at the eye-level of the medical professional 124 or may be manually adjusted according to the preferences of the medical professional 124 via the gooseneck support mechanism 422. The floating camera component 420 may further interact with the retractable camera device 304 within the interior chamber 300 of the patient station 110, which comprises a retina scanner and image processing unit configured to detect a position of the eyes or any other body part of the patient 114 and automatically readjust the camera at the applicable body part level of the patient 114. The gooseneck support mechanism 422 is configured to allow swiveling, rotating, or any other necessary movements to support an optimal view of the medical professional 124.

The adjustable platform 404 may further comprise an extendable electrical wire configured to plug into electric sources within the remote medical facility space 400 in order to power the medical facility clinician device 122, and other electrical components. The first user indicator component 406 and the second user indicator component serve the purpose of indicating the status, title, type, or designation of the medical professional 124 currently engaged in the session with the patient 114, and are communicatively coupled to what is projected to the patient 114 via the projector. For example, during the beginning of a session the patient 114 interacts with the medical professional 124 where the background (shade or hint of color integrated with the projected image of the medical professional) is the first user indicator component 406, which is color-coded green (for example, by emitting a green light) indicating that the medical professional 124 is a nurse who may be simply requesting or analyzing body vitals acquired via biometric/vitals measuring device 306. During the latter part of the session, the background is the second user indicator component, which is color-coded red (for example, by emitting a red light) indicating that the medical professional 124 is a doctor. In one embodiment, the user indicator components 406 and the second user indicator component may be symbol-coded, graphic-coded, or any other means suitable to indicate a distinction between two separate individuals.

The remote medical facility interactive interface 412 and the floating camera component 420 may be communicatively coupled to the retractable camera device 304 for the purpose of providing images and videos of the patient 114 in real-time. The acquired images, videos, and other information of the patient 114 acquired via components within the interior chamber 300 may be displayed on the remote medical facility interactive interface 412 and/or the medical facility clinician device 122. The purpose of the integration of the medical facility clinician device 122 and the remote medical facility interactive interface 412 is to allow the session to include a plurality of medical professionals 124 to examine, diagnose, and treat the patient 114 within a single session while supporting communicative coupling via the network 102. The network 102 supports the establishment of a real time telemedicine session between the patient 114 and the medical professional 124 via components of the interior chamber 300 and the floating camera component 420 and the remote medical facility space 400, and is configured to store any data derived from the patient 114 or the medical professional 124. Upon proper authentication and receiving of necessary information from the patient 114, the medical professional 124 is able to utilize the combination of the components within the patient station 110, the medical facility clinician device 122, the kiosk inventory storage component 206, and the remote medical facility interactive interface 412 to extract, examine, diagnose, and treat the patient 114 via providing a plurality of instructions configured to interact with the patient client device 112 resulting in an effective manner while maintaining the patient 114 within the interior chamber 300.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A method comprising:
   collecting, by a computing device from a patient in a medical services kiosk on an electronic communication network, medical information, and the medical information includes biometric measurements obtained by biometric devices in the medical services kiosk;
   transmitting, by the computing device to a clinician station in remote communication with the patient by the electronic communication network, the medical information upon initiating remote session;
   displaying a first colored light associated with an intake person from the clinician station that is visible in the medical services kiosk;
   facilitating a communicative interlink with a healthcare professional needed according to data inputted by the intake person;
   displaying the healthcare professional on a display device in the medical services kiosk automatically after initiating the remote session;
   displaying a second colored light associated with the healthcare professional from the clinician station that is visible to the patient in the medical services kiosk, the healthcare professional being different than the intake person; and
   setting a privacy window of the medical services kiosk to an opaque mode inhibiting a view into an interior chamber of the medical services kiosk from an exterior area.

2. The method of claim 1, wherein the medical information comprises one of a weight, blood pressure, and temperature.

3. The method of claim 1, further comprising:
   transmitting, by the medical services kiosk, a plurality of images, videos, and audio to the clinician station; and
   the first colored light and the second colored light are associated with different backgrounds on the display device.

4. The method of claim 1, further comprising transmitting a prescription for a medication for the patient to the medical services kiosk.

5. The method of claim 4, wherein the medical services kiosk includes a medication storage component, the method further comprising:
   sending instructions to the medical services kiosk to dispense the medication from the medication storage component to the patient; and
   verifying the medication using a camera in the medical services kiosk.

6. The method of claim 1, wherein displaying the healthcare professional on the display device comprises displaying the healthcare professional on a life-size dimension and a face-to-face screen.

7. A non-transitory storage media storing instructions which, when executed by a processor, cause the processor to:
   collect, from a patient in a medical services kiosk on an electronic communication network, medical information, and the medical information includes biometric measurements obtained by biometric devices in the medical services kiosk;
   set a privacy window of the medical services kiosk to an opaque mode that inhibits a view into an interior chamber of the medical services kiosk from an exterior area;
   transmit, to a clinician station in remote communication with the patient by the electronic communication network, the medical information upon initiating a remote session;
   display a first colored light associated with an intake person from the clinician station that is visible in the medical services kiosk;
   facilitate a communicative interlink with a healthcare professional needed according to data inputted by the intake;
   display the healthcare professional on a display device in the medical services kiosk automatically after initiating the remote session; and
   display a second colored light associated with the healthcare professional from the clinician station that is visible to the patient in the medical services kiosk, the healthcare professional being different than the intake person.

8. The non-transitory storage media of claim 7, further storing instructions that, when executed by the processor, cause the processor to:
   receive instructions via a medicine storage component of the medical services kiosk for dispensing medication to the patient.

9. The non-transitory storage media of claim 8, further storing instructions that, when executed by the processor, cause the processor to:
   verify the medication using a camera in the medical services kiosk.

10. The non-transitory storage media of claim 7, wherein the medical information comprises one of a weight, blood pressure, and temperature of the patient.

11. The non-transitory storage media of claim 7, further storing instructions that, when executed by the processor, cause the processor to:
    transmit, by the medical services kiosk, a plurality of images, videos, and audio to the clinician station; and
    the first colored light and the second colored light are associate with different backgrounds on the display device.

12. A system comprising:

a processor; and a memory storing instructions that, when executed by the processor, cause the processor to:

set a privacy window of a medical services kiosk to an opaque mode that inhibits a view into an interior chamber from an exterior area;

collect, from a patient in the medical services kiosk on an electronic communication network, medical information that includes biometric measurements obtained by biometric devices in the medical services kiosk;

transmit, to a station in remote communication with the patient by the electronic communication network, the medical information upon initiating a remote session;

display a first symbol associated with an intake person from the station in the medical services kiosk;

facilitate a communicative communicative interlink with a healthcare professional needed according to data inputted by the intake person;

display the healthcare professional on a display device in the medical services kiosk automatically during the remote session; and display a second symbol associated with the healthcare professional from the station in the medical services kiosk, and the first symbol and the second symbol are different and the healthcare professional is different than the intake person.

13. The system of claim 12, further including instructions to:

receive instructions via a medicine storage component of the medical services kiosk for dispensing medication to the patient.

14. The system of claim 13, further including instructions to:

verify the medication using a camera in the medical services kiosk.

15. The system of claim 12, wherein the medical information comprises one of a weight, blood pressure, and temperature.

16. The system of claim 12, further including instructions to:

transmit, by the medical services kiosk, a plurality of images, videos, and audio to the station; and the first symbol and the second symbol are associated with different backgrounds on the display device.

* * * * *